(12) United States Patent
Vogelstein et al.

(10) Patent No.: US 7,745,165 B2
(45) Date of Patent: Jun. 29, 2010

(54) PHOSPHATASE ASSOCIATED WITH METASTASIS

(75) Inventors: Bert Vogelstein, Baltimore, MD (US); Kenneth W. Kinzler, Bel Air, MD (US); Saurabh Saha, New York, NY (US); Alberto Bardelli, Turin (IT)

(73) Assignee: The John Hopkins University, Baltimore, MD (US)

( * ) Notice: Subject to any disclaimer, the term of this patent is extended or adjusted under 35 U.S.C. 154(b) by 1159 days.

(21) Appl. No.: 10/868,658

(22) Filed: Jun. 16, 2004

(65) Prior Publication Data

US 2005/0047996 A1    Mar. 3, 2005

Related U.S. Application Data

(63) Continuation of application No. PCT/US02/31247, filed on Oct. 2, 2002.

(60) Provisional application No. 60/327,332, filed on Oct. 9, 2001.

(51) Int. Cl.
C12Q 1/48 (2006.01)
G01N 33/567 (2006.01)

(52) U.S. Cl. ............................. 435/21; 435/4

(58) Field of Classification Search ............ 435/4, 435/21
See application file for complete search history.

(56) References Cited

U.S. PATENT DOCUMENTS

| | | | |
|---|---|---|---|
| 5,602,171 A | 2/1997 | Tang et al. | |
| 5,843,481 A | 12/1998 | Cruz | |
| 6,020,179 A | 2/2000 | Goli et al. | |
| 6,022,541 A | 2/2000 | Senger et al. | |
| 6,258,582 B1 * | 7/2001 | Acton ................ | 435/196 |
| 6,261,535 B1 | 7/2001 | Thorpe et al. | |
| 6,432,941 B1 * | 8/2002 | Uckun et al. ........ | 514/185 |

FOREIGN PATENT DOCUMENTS

| | | |
|---|---|---|
| WO | WO 97/06262 A | 2/1997 |
| WO | 97/47296 | 12/1997 |
| WO | 00/57860 | 5/2000 |
| WO | 01/12180 | 2/2001 |

OTHER PUBLICATIONS

Peng, L. et al., Biochemical and Biophysical Research Communications, 342: 179-183, 2006.*
Bessette, D.C., et al., Cells Tissues Organs, 185(1-3): 232-236, 2007; abstract only.*
Cheng, J. D. et al., Cancer Research 62: 4767-4772, 2002.*
ATCC Catalog pages for CRL-1573 (HEK293 cells), 2008.*
Takenaga, K. et al. Invasion Metastasis, 16: 97-106, 1996.*
Cruz, T.F. et al. Molecular and Cellular Biochemistry, 153: 161-166, 1995.*
S. Saha et al., "Phosphatase Associated With Metastasis of Colorectal Cancer," Nov. 9, 2001, Science, American Association for the Advancement of Science, U.S., pp. 1343-1346, vol. 294.
J. Bradbury, "Metastasis in Colorectal Cancer Associated With Phosphatase Expression," Lancet, Oct. 13, 2001, p. 1245, Lancet, vol. 358, No. 9289.
W. F. Matter et al., "Role of PRL-3, a Human Muscle-Specific Tyrosine Phosphatase, in Angiotensin-II Signaling," Biochemical and Biophysical Research Communications, Academic Press, San Diego, CA, U.S., May 25, 2001, pp. 1061-1068, vol. 283, No. 5.
R. H. Diamond, "PRL-1, a Unique Nuclear Protein Tyrosine Phosphatase, Affects Cell Growth," Jun. 1, 1994, Molecular and Cellular Biology, Washington, D.C., U.S., pp. 3752-3762, vol. 14, No. 6.
C. A. Cates, "Prenylation of Oncogenic Human PTPCAAX Protein Tyrosine Phosphatases," Dec. 20, 1996, pp.
J. Marx "New Insights into Metastasis," Science, Oct. 12, 2001, pp. 281-282, vol. 294.
Qi Zeng et al., "Prenylation-Dependent Association of Protein-Tyrosine Phosphatases PRL-1, -2, and -3 with the Plasma Membrane and the Early Endosome," Jul. 14, 2000, The Journal of Biological Chemistry, pp. 21444-21452, vol. 275, No. 28.
J. C. Alers, "Interphase Cytogenetics of Prostatic Tumor Progression: Specific Chromosomal Abnormalities Are Involved in Metastasis to the Bone," Nov. 1997, Laboratory Investigations, pp. 437-448, vol. 77, No. 5.
N. N. Nupponen, "Mapping the Amplification of EIF353 in Breast and Prostate Cancer," 2000, Genes, Chromosomes & Cancer, pp. 204-210.
Ahmed El Gedaily et al., "Discovery of New DNA Amplification Loci in Prostate Cancer by Comparative Genomic Hybridization," 2001, The Prostate, pp. 184-190.
A. Paredes-Zaglul, "Analysis of Colorectal Cancer by Comparative Genomic Hybridization: Evidence for Induction of the Metastatic Phenotype by Loss of Tumor Suppressor Genes," Apr. 1998, Clinical Cancer Research, pp. 879-886, vol. 4.
B. I. Posner et al., "Peroxovanadium Compounds," Feb. 11, 1994; The Journal of Biological Chemistry, pp. 4596-4604, vol. 289, No. 6.
J. Li et al., "Generation of PRL-3- and PRL-1-Specific Monoclonal Antibodies as Potential Diagnostic Markers for Cancer Metastases," Clinical Cancer Research, Mar. 15, 2005, vol. 11, pp. 2195-2204.
Guo et al., "Anti-PRL-3 Antibody Produced in Rabbit, IgG Fraction of Antiserum, Buffered Aqueous Solution," Landes Bioscience, May 5, 2008, vol. 7, No. 5, 4 pages.
C. Djordjevic et al., "Antitumor Activity and Toxicity of Peroxo Heteroligand Vanadates(V) in Relation to Biochemistry of Vanadium," Journal of Inorganic Biochemistry, 1985, vol. 25, pp. 51-55.
A. Morinville et al., "From Vanadis to Atropos: Vanadium Compounds as Pharmacological Tools in Cell Death Signalling," TiPS, Nov. 1998, vol. 19, pp. 452-460.
EP Office Action dated Nov. 11, 2009.

* cited by examiner

*Primary Examiner*—Alan M. Harris
*Assistant Examiner*—Anne L Holleran

(57) ABSTRACT

Among the genes identified, in a comparison of the global gene expression profile of metastatic colorectal cancer to that of primary cancers, benign colorectal tumors, and normal colorectal epithelium, the PRL-3 protein tyrosine phosphatase gene was of particular interest. It was expressed at high levels in each of 18 cancer metastases studied but at lower levels in non-metastatic tumors and normal colorectal epithelium. In three of twelve metastases examined, multiple copies of the PRL-3 gene were found within a small amplicon located at chromosome 8q24.3. These data suggest that the PRL-3 gene is important for colorectal cancer metastasis and provides a new therapeutic target for these intractable lesions.

19 Claims, 4 Drawing Sheets

SEQUENCE LISTING

<160> NUMBER OF SEQ ID NOS: 190

<210> SEQ ID NO 1
<211> LENGTH: 20
<212> TYPE: DNA
<213> ORGANISM: Homo sapiens

<400> SEQUENCE: 1
cctcacagaa cttggccttc                                                  20

<210> SEQ ID NO 2
<211> LENGTH: 20
<212> TYPE: DNA
<213> ORGANISM: Homo sapiens

<400> SEQUENCE: 2
gcctctctac cctccctcag                                                  20

<210> SEQ ID NO 3
<211> LENGTH: 20
<212> TYPE: DNA
<213> ORGANISM: Homo sapiens

<400> SEQUENCE: 3
gggcttccct aagcacaaat                                                  20

<210> SEQ ID NO 4
<211> LENGTH: 20
<212> TYPE: DNA
<213> ORGANISM: Homo sapiens

<400> SEQUENCE: 4
ttaggcggag tcttgaggaa                                                  20

```
<210> SEQ ID NO 5
<211> LENGTH: 10
<212> TYPE: DNA
<213> ORGANISM: Homo sapiens

<400> SEQUENCE: 5
taggtcagga                                                          10

<210> SEQ ID NO 6
<211> LENGTH: 10
<212> TYPE: DNA
<213> ORGANISM: Homo sapiens

<400> SEQUENCE: 6
tgattggttt                                                          10

<210> SEQ ID NO 7
<211> LENGTH: 10
<212> TYPE: DNA
<213> ORGANISM: Homo sapiens

<400> SEQUENCE: 7
ggaatatgca                                                          10

<210> SEQ ID NO 8
<211> LENGTH: 10
<212> TYPE: DNA
<213> ORGANISM: Homo sapiens

<400> SEQUENCE: 8
aatcttgttt                                                          10

<210> SEQ ID NO 9
<211> LENGTH: 10
<212> TYPE: DNA
<213> ORGANISM: Homo sapiens

<400> SEQUENCE: 9
gtcttcttaa                                                          10

<210> SEQ ID NO 10
<211> LENGTH: 10
<212> TYPE: DNA
<213> ORGANISM: Homo sapiens

<400> SEQUENCE: 10
ataataaaag                                                          10

<210> SEQ ID NO 11
<211> LENGTH: 10
<212> TYPE: DNA
<213> ORGANISM: Homo sapiens

<400> SEQUENCE: 11
taaatatgga                                                          10

<210> SEQ ID NO 12
<211> LENGTH: 10
<212> TYPE: DNA
<213> ORGANISM: Homo sapiens

<400> SEQUENCE: 12
```
atttttgtat                                                                         10

<210> SEQ ID NO 13
<211> LENGTH: 10
<212> TYPE: DNA
<213> ORGANISM: Homo sapiens

<400> SEQUENCE: 13
tagctggaaa                                                                         10

<210> SEQ ID NO 14
<211> LENGTH: 10
<212> TYPE: DNA
<213> ORGANISM: Homo sapiens

<400> SEQUENCE: 14
ggagggctgg                                                                         10

<210> SEQ ID NO 15
<211> LENGTH: 10
<212> TYPE: DNA
<213> ORGANISM: Homo sapiens

<400> SEQUENCE: 15
gtcagtcact                                                                         10

<210> SEQ ID NO 16
<211> LENGTH: 10
<212> TYPE: DNA
<213> ORGANISM: Homo sapiens

<400> SEQUENCE: 16
ttgagtagga                                                                         10

<210> SEQ ID NO 17
<211> LENGTH: 10
<212> TYPE: DNA
<213> ORGANISM: Homo sapiens

<400> SEQUENCE: 17
tgggggccga                                                                         10

<210> SEQ ID NO 18
<211> LENGTH: 10
<212> TYPE: DNA
<213> ORGANISM: Homo sapiens

<400> SEQUENCE: 18
tgggctgggg                                                                         10

<210> SEQ ID NO 19
<211> LENGTH: 10
<212> TYPE: DNA
<213> ORGANISM: Homo sapiens

<400> SEQUENCE: 19
tagctggaac                                                                         10

<210> SEQ ID NO 20
<211> LENGTH: 10
<212> TYPE: DNA
<213> ORGANISM: Homo sapiens

<400> SEQUENCE: 20

-continued cttccttgcc                                                         10

<210> SEQ ID NO 21
<211> LENGTH: 10
<212> TYPE: DNA
<213> ORGANISM: Homo sapiens

<400> SEQUENCE: 21
gcggcagtta                                                         10

<210> SEQ ID NO 22
<211> LENGTH: 10
<212> TYPE: DNA
<213> ORGANISM: Homo sapiens

<400> SEQUENCE: 22
ctgcacttac                                                         10

<210> SEQ ID NO 23
<211> LENGTH: 10
<212> TYPE: DNA
<213> ORGANISM: Homo sapiens

<400> SEQUENCE: 23
aagctgttta                                                         10

<210> SEQ ID NO 24
<211> LENGTH: 10
<212> TYPE: DNA
<213> ORGANISM: Homo sapiens

<400> SEQUENCE: 24
gtgagggcta                                                         10

<210> SEQ ID NO 25
<211> LENGTH: 10
<212> TYPE: DNA
<213> ORGANISM: Homo sapiens

<400> SEQUENCE: 25
ggggctgtat                                                         10

<210> SEQ ID NO 26
<211> LENGTH: 10
<212> TYPE: DNA
<213> ORGANISM: Homo sapiens

<400> SEQUENCE: 26
ctggaggctg                                                         10

<210> SEQ ID NO 27
<211> LENGTH: 10
<212> TYPE: DNA
<213> ORGANISM: Homo sapiens

<400> SEQUENCE: 27
ggctgggttt                                                         10

<210> SEQ ID NO 28
<211> LENGTH: 10
<212> TYPE: DNA
<213> ORGANISM: Homo sapiens -continued

```
<400> SEQUENCE: 28
gggggtgggt                                                            10

<210> SEQ ID NO 29
<211> LENGTH: 10
<212> TYPE: DNA
<213> ORGANISM: Homo sapiens

<400> SEQUENCE: 29
cagcatctaa                                                            10

<210> SEQ ID NO 30
<211> LENGTH: 10
<212> TYPE: DNA
<213> ORGANISM: Homo sapiens

<400> SEQUENCE: 30
tttccaatct                                                            10

<210> SEQ ID NO 31
<211> LENGTH: 10
<212> TYPE: DNA
<213> ORGANISM: Homo sapiens

<400> SEQUENCE: 31
tttctagggg                                                            10

<210> SEQ ID NO 32
<211> LENGTH: 10
<212> TYPE: DNA
<213> ORGANISM: Homo sapiens

<400> SEQUENCE: 32
aaagtgaaga                                                            10

<210> SEQ ID NO 33
<211> LENGTH: 10
<212> TYPE: DNA
<213> ORGANISM: Homo sapiens

<400> SEQUENCE: 33
tttgcacttg                                                            10

<210> SEQ ID NO 34
<211> LENGTH: 10
<212> TYPE: DNA
<213> ORGANISM: Homo sapiens

<400> SEQUENCE: 34
cctggaatga                                                            10

<210> SEQ ID NO 35
<211> LENGTH: 10
<212> TYPE: DNA
<213> ORGANISM: Homo sapiens

<400> SEQUENCE: 35
ggaggtaggg                                                            10

<210> SEQ ID NO 36
<211> LENGTH: 10
<212> TYPE: DNA
<213> ORGANISM: Homo sapiens
```

```
<400> SEQUENCE: 36
ctgtacttgt                                                              10

<210> SEQ ID NO 37
<211> LENGTH: 10
<212> TYPE: DNA
<213> ORGANISM: Homo sapiens

<400> SEQUENCE: 37
tccttgcttc                                                              10

<210> SEQ ID NO 38
<211> LENGTH: 10
<212> TYPE: DNA
<213> ORGANISM: Homo sapiens

<400> SEQUENCE: 38
tatctgtcta                                                              10

<210> SEQ ID NO 39
<211> LENGTH: 10
<212> TYPE: DNA
<213> ORGANISM: Homo sapiens

<400> SEQUENCE: 39
ttagataagc                                                              10

<210> SEQ ID NO 40
<211> LENGTH: 10
<212> TYPE: DNA
<213> ORGANISM: Homo sapiens

<400> SEQUENCE: 40
agtggaggga                                                              10

<210> SEQ ID NO 41
<211> LENGTH: 10
<212> TYPE: DNA
<213> ORGANISM: Homo sapiens

<400> SEQUENCE: 41
tgcagatatt                                                              10

<210> SEQ ID NO 42
<211> LENGTH: 10
<212> TYPE: DNA
<213> ORGANISM: Homo sapiens

<400> SEQUENCE: 42
gggaggggtg                                                              10

<210> SEQ ID NO 43
<211> LENGTH: 10
<212> TYPE: DNA
<213> ORGANISM: Homo sapiens

<400> SEQUENCE: 43
taggtcagga                                                              10

<210> SEQ ID NO 44
<211> LENGTH: 10
<212> TYPE: DNA
```

<213> ORGANISM: Homo sapiens

<400> SEQUENCE: 44
tgattggttt          10

<210> SEQ ID NO 45
<211> LENGTH: 10
<212> TYPE: DNA
<213> ORGANISM: Homo sapiens

<400> SEQUENCE: 45
ggaatatgca          10

<210> SEQ ID NO 46
<211> LENGTH: 10
<212> TYPE: DNA
<213> ORGANISM: Homo sapiens

<400> SEQUENCE: 46
aatcttgttt          10

<210> SEQ ID NO 47
<211> LENGTH: 10
<212> TYPE: DNA
<213> ORGANISM: Homo sapiens

<400> SEQUENCE: 47
gtcttcttaa          10

<210> SEQ ID NO 48
<211> LENGTH: 10
<212> TYPE: DNA
<213> ORGANISM: Homo sapiens

<400> SEQUENCE: 48
ataataaaag          10

<210> SEQ ID NO 49
<211> LENGTH: 10
<212> TYPE: DNA
<213> ORGANISM: Homo sapiens

<400> SEQUENCE: 49
taaatatgga          10

<210> SEQ ID NO 50
<211> LENGTH: 10
<212> TYPE: DNA
<213> ORGANISM: Homo sapiens

<400> SEQUENCE: 50
atttttgtat          10

<210> SEQ ID NO 51
<211> LENGTH: 10
<212> TYPE: DNA
<213> ORGANISM: Homo sapiens

<400> SEQUENCE: 51
tagctggaaa          10

<210> SEQ ID NO 52
<211> LENGTH: 10

-continued

```
<212> TYPE: DNA
<213> ORGANISM: Homo sapiens

<400> SEQUENCE: 52
ggagggctgg                                                          10

<210> SEQ ID NO 53
<211> LENGTH: 10
<212> TYPE: DNA
<213> ORGANISM: Homo sapiens

<400> SEQUENCE: 53
gtcagtcact                                                          10

<210> SEQ ID NO 54
<211> LENGTH: 10
<212> TYPE: DNA
<213> ORGANISM: Homo sapiens

<400> SEQUENCE: 54
ttgagtagga                                                          10

<210> SEQ ID NO 55
<211> LENGTH: 10
<212> TYPE: DNA
<213> ORGANISM: Homo sapiens

<400> SEQUENCE: 55
tgggggccga                                                          10

<210> SEQ ID NO 56
<211> LENGTH: 10
<212> TYPE: DNA
<213> ORGANISM: Homo sapiens

<400> SEQUENCE: 56
tgggctgggg                                                          10

<210> SEQ ID NO 57
<211> LENGTH: 10
<212> TYPE: DNA
<213> ORGANISM: Homo sapiens

<400> SEQUENCE: 57
tagctggaac                                                          10

<210> SEQ ID NO 58
<211> LENGTH: 10
<212> TYPE: DNA
<213> ORGANISM: Homo sapiens

<400> SEQUENCE: 58
cttccttgcc                                                          10

<210> SEQ ID NO 59
<211> LENGTH: 10
<212> TYPE: DNA
<213> ORGANISM: Homo sapiens

<400> SEQUENCE: 59
gcggcagtta                                                          10

<210> SEQ ID NO 60
```

```
<211> LENGTH: 10
<212> TYPE: DNA
<213> ORGANISM: Homo sapiens

<400> SEQUENCE: 60
ctgcacttac                                                              10

<210> SEQ ID NO 61
<211> LENGTH: 10
<212> TYPE: DNA
<213> ORGANISM: Homo sapiens

<400> SEQUENCE: 61
aagctgttta                                                              10

<210> SEQ ID NO 62
<211> LENGTH: 10
<212> TYPE: DNA
<213> ORGANISM: Homo sapiens

<400> SEQUENCE: 62
gtgagggcta                                                              10

<210> SEQ ID NO 63
<211> LENGTH: 10
<212> TYPE: DNA
<213> ORGANISM: Homo sapiens

<400> SEQUENCE: 63
ggggctgtat                                                              10

<210> SEQ ID NO 64
<211> LENGTH: 10
<212> TYPE: DNA
<213> ORGANISM: Homo sapiens

<400> SEQUENCE: 64
ctggaggctg                                                              10

<210> SEQ ID NO 65
<211> LENGTH: 10
<212> TYPE: DNA
<213> ORGANISM: Homo sapiens

<400> SEQUENCE: 65
ggctgggttt                                                              10

<210> SEQ ID NO 66
<211> LENGTH: 10
<212> TYPE: DNA
<213> ORGANISM: Homo sapiens

<400> SEQUENCE: 66
gggggtgggt                                                              10

<210> SEQ ID NO 67
<211> LENGTH: 10
<212> TYPE: DNA
<213> ORGANISM: Homo sapiens

<400> SEQUENCE: 67
cagcatctaa                                                              10
```

```
<210> SEQ ID NO 68
<211> LENGTH: 10
<212> TYPE: DNA
<213> ORGANISM: Homo sapiens

<400> SEQUENCE: 68
tttccaatct                                                                  10

<210> SEQ ID NO 69
<211> LENGTH: 10
<212> TYPE: DNA
<213> ORGANISM: Homo sapiens

<400> SEQUENCE: 69
tttctagggg                                                                  10

<210> SEQ ID NO 70
<211> LENGTH: 10
<212> TYPE: DNA
<213> ORGANISM: Homo sapiens

<400> SEQUENCE: 70
aaagtgaaga                                                                  10

<210> SEQ ID NO 71
<211> LENGTH: 10
<212> TYPE: DNA
<213> ORGANISM: Homo sapiens

<400> SEQUENCE: 71
tttgcacttg                                                                  10

<210> SEQ ID NO 72
<211> LENGTH: 10
<212> TYPE: DNA
<213> ORGANISM: Homo sapiens

<400> SEQUENCE: 72
cctggaatga                                                                  10

<210> SEQ ID NO 73
<211> LENGTH: 10
<212> TYPE: DNA
<213> ORGANISM: Homo sapiens

<400> SEQUENCE: 73
ggaggtaggg                                                                  10

<210> SEQ ID NO 74
<211> LENGTH: 10
<212> TYPE: DNA
<213> ORGANISM: Homo sapiens

<400> SEQUENCE: 74
ctgtacttgt                                                                  10

<210> SEQ ID NO 75
<211> LENGTH: 10
<212> TYPE: DNA
<213> ORGANISM: Homo sapiens

<400> SEQUENCE: 75
tccttgcttc                                                                  10
```

<210> SEQ ID NO 76
<211> LENGTH: 10
<212> TYPE: DNA
<213> ORGANISM: Homo sapiens

<400> SEQUENCE: 76
tatctgtcta                                                          10

<210> SEQ ID NO 77
<211> LENGTH: 10
<212> TYPE: DNA
<213> ORGANISM: Homo sapiens

<400> SEQUENCE: 77
ttagataagc                                                          10

<210> SEQ ID NO 78
<211> LENGTH: 10
<212> TYPE: DNA
<213> ORGANISM: Homo sapiens

<400> SEQUENCE: 78
agtggaggga                                                          10

<210> SEQ ID NO 79
<211> LENGTH: 10
<212> TYPE: DNA
<213> ORGANISM: Homo sapiens

<400> SEQUENCE: 79
tgcagatatt                                                          10

<210> SEQ ID NO 80
<211> LENGTH: 10
<212> TYPE: DNA
<213> ORGANISM: Homo sapiens

<400> SEQUENCE: 80
gggaggggtg                                                          10

<210> SEQ ID NO 81
<211> LENGTH: 20
<212> TYPE: DNA
<213> ORGANISM: Homo sapiens

<400> SEQUENCE: 81
agccccgtac ttcttcaggt                                               20

<210> SEQ ID NO 82
<211> LENGTH: 20
<212> TYPE: DNA
<213> ORGANISM: Homo sapiens

<400> SEQUENCE: 82 ctccacccctt gaattcctga                                              20

<210> SEQ ID NO 83
<211> LENGTH: 20
<212> TYPE: DNA
<213> ORGANISM: Homo sapiens

<400> SEQUENCE: 83
cccagttctg ggctatttga                                               20

```
<210> SEQ ID NO 84
<211> LENGTH: 20
<212> TYPE: DNA
<213> ORGANISM: Homo sapiens

<400> SEQUENCE: 84
aggcaatttc ttgcaaccac                                              20

<210> SEQ ID NO 85
<211> LENGTH: 20
<212> TYPE: DNA
<213> ORGANISM: Homo sapiens

<400> SEQUENCE: 85
ccagcaggga ctggtaagaa                                              20

<210> SEQ ID NO 86
<211> LENGTH: 20
<212> TYPE: DNA
<213> ORGANISM: Homo sapiens

<400> SEQUENCE: 86
gcagggaatt cacctcaaga                                              20

<210> SEQ ID NO 87
<211> LENGTH: 20
<212> TYPE: DNA
<213> ORGANISM: Homo sapiens

<400> SEQUENCE: 87
aggggctgat tcacttcctt                                              20

<210> SEQ ID NO 88
<211> LENGTH: 20
<212> TYPE: DNA
<213> ORGANISM: Homo sapiens

<400> SEQUENCE: 88
aagagcaaat gagccaaacg                                              20

<210> SEQ ID NO 89
<211> LENGTH: 20
<212> TYPE: DNA
<213> ORGANISM: Homo sapiens

<400> SEQUENCE: 89
cacagcttgc ttgtcgatgt                                              20

<210> SEQ ID NO 90
<211> LENGTH: 20
<212> TYPE: DNA
<213> ORGANISM: Homo sapiens

<400> SEQUENCE: 90
tcccgaagat gaaatgaagg                                              20

<210> SEQ ID NO 91
<211> LENGTH: 20
<212> TYPE: DNA
<213> ORGANISM: Homo sapiens

<400> SEQUENCE: 91
```
tgagccagct gaaaacactg                                           20

<210> SEQ ID NO 92
<211> LENGTH: 20
<212> TYPE: DNA
<213> ORGANISM: Homo sapiens

<400> SEQUENCE: 92
tgctgaatgt gatcggagaa                                           20

<210> SEQ ID NO 93
<211> LENGTH: 20
<212> TYPE: DNA
<213> ORGANISM: Homo sapiens

<400> SEQUENCE: 93
tgagtctcat ccccatctcc                                           20

<210> SEQ ID NO 94
<211> LENGTH: 20
<212> TYPE: DNA
<213> ORGANISM: Homo sapiens

<400> SEQUENCE: 94
actggctggt aggtcccttt                                           20

<210> SEQ ID NO 95
<211> LENGTH: 19
<212> TYPE: DNA
<213> ORGANISM: Homo sapiens

<400> SEQUENCE: 95
atagggcagg tggcatgtt                                            19

<210> SEQ ID NO 96
<211> LENGTH: 20
<212> TYPE: DNA
<213> ORGANISM: Homo sapiens

<400> SEQUENCE: 96
cggagacaga gaaccgctac                                           20

<210> SEQ ID NO 97
<211> LENGTH: 20
<212> TYPE: DNA
<213> ORGANISM: Homo sapiens

<400> SEQUENCE: 97
gtgcagacaa tgctgtgctt                                           20

<210> SEQ ID NO 98
<211> LENGTH: 20
<212> TYPE: DNA
<213> ORGANISM: Homo sapiens

<400> SEQUENCE: 98
cggtgctggt agaaggagag                                           20

<210> SEQ ID NO 99
<211> LENGTH: 20
<212> TYPE: DNA
<213> ORGANISM: Homo sapiens

<400> SEQUENCE: 99
ggcagacaga cagacacagc                                                20

<210> SEQ ID NO 100
<211> LENGTH: 20
<212> TYPE: DNA
<213> ORGANISM: Homo sapiens

<400> SEQUENCE: 100
acaaggtgta tgcggagagg                                                20

<210> SEQ ID NO 101
<211> LENGTH: 20
<212> TYPE: DNA
<213> ORGANISM: Homo sapiens

<400> SEQUENCE: 101
ggccctgtac aaccagcata                                                20

<210> SEQ ID NO 102
<211> LENGTH: 20
<212> TYPE: DNA
<213> ORGANISM: Homo sapiens

<400> SEQUENCE: 102
cccagctcta gactgccaag                                                20

<210> SEQ ID NO 103
<211> LENGTH: 20
<212> TYPE: DNA
<213> ORGANISM: Homo sapiens

<400> SEQUENCE: 103
gaggcttctg caatcctgag                                                20

<210> SEQ ID NO 104
<211> LENGTH: 20
<212> TYPE: DNA
<213> ORGANISM: Homo sapiens

<400> SEQUENCE: 104
ggagccatgg agagtgactt                                                20

<210> SEQ ID NO 105
<211> LENGTH: 20
<212> TYPE: DNA
<213> ORGANISM: Homo sapiens

<400> SEQUENCE: 105
ttggggagtt ttgccattac                                                20

<210> SEQ ID NO 106
<211> LENGTH: 20
<212> TYPE: DNA
<213> ORGANISM: Homo sapiens

<400> SEQUENCE: 106
gggcagaatc atcacgaagt                                                20

<210> SEQ ID NO 107
<211> LENGTH: 20
<212> TYPE: DNA
<213> ORGANISM: Homo sapiens

<400> SEQUENCE: 107
tctccgttct ctgggtaagg                                                      20

<210> SEQ ID NO 108
<211> LENGTH: 20
<212> TYPE: DNA
<213> ORGANISM: Homo sapiens

<400> SEQUENCE: 108
tcccaccctc aatatcctca                                                      20

<210> SEQ ID NO 109
<211> LENGTH: 20
<212> TYPE: DNA
<213> ORGANISM: Homo sapiens

<400> SEQUENCE: 109
agaccttcag caatggcact                                                      20

<210> SEQ ID NO 110
<211> LENGTH: 20
<212> TYPE: DNA
<213> ORGANISM: Homo sapiens

<400> SEQUENCE: 110
agggagagtc cctccactgt                                                      20

<210> SEQ ID NO 111
<211> LENGTH: 20
<212> TYPE: DNA
<213> ORGANISM: Homo sapiens

<400> SEQUENCE: 111
ctgaagaagc cccaagacag                                                      20

<210> SEQ ID NO 112
<211> LENGTH: 20
<212> TYPE: DNA
<213> ORGANISM: Homo sapiens

<400> SEQUENCE: 112
attggaattt ctggcctcct                                                      20

<210> SEQ ID NO 113
<211> LENGTH: 20
<212> TYPE: DNA
<213> ORGANISM: Homo sapiens

<400> SEQUENCE: 113
agcctctgtc atgaggaacg                                                      20

<210> SEQ ID NO 114
<211> LENGTH: 20
<212> TYPE: DNA
<213> ORGANISM: Homo sapiens

<400> SEQUENCE: 114
gggagcaagt tgcagtcttt                                                      20

<210> SEQ ID NO 115
<211> LENGTH: 20
<212> TYPE: DNA
<213> ORGANISM: Homo sapiens -continued

```
<400> SEQUENCE: 115
gccctgaatt cttttgacga                                              20

<210> SEQ ID NO 116
<211> LENGTH: 20
<212> TYPE: DNA
<213> ORGANISM: Homo sapiens

<400> SEQUENCE: 116
tgagggttct ggcttactgg                                              20

<210> SEQ ID NO 117
<211> LENGTH: 20
<212> TYPE: DNA
<213> ORGANISM: Homo sapiens

<400> SEQUENCE: 117
ccgcccagtt caatacaaac                                              20

<210> SEQ ID NO 118
<211> LENGTH: 20
<212> TYPE: DNA
<213> ORGANISM: Homo sapiens

<400> SEQUENCE: 118
catggcaccc ttttaccagt                                              20

<210> SEQ ID NO 119
<211> LENGTH: 20
<212> TYPE: DNA
<213> ORGANISM: Homo sapiens

<400> SEQUENCE: 119
gggacttctc aggtcgtgtc                                              20

<210> SEQ ID NO 120
<211> LENGTH: 20
<212> TYPE: DNA
<213> ORGANISM: Homo sapiens

<400> SEQUENCE: 120
ttgcgcacac acacaaaata                                              20

<210> SEQ ID NO 121
<211> LENGTH: 20
<212> TYPE: DNA
<213> ORGANISM: Homo sapiens

<400> SEQUENCE: 121
agcagtggca tagcaaggat                                              20

<210> SEQ ID NO 122
<211> LENGTH: 20
<212> TYPE: DNA
<213> ORGANISM: Homo sapiens

<400> SEQUENCE: 122
caccaaaggg aggaggtaca                                              20

<210> SEQ ID NO 123
<211> LENGTH: 20
<212> TYPE: DNA
```

<213> ORGANISM: Homo sapiens

<400> SEQUENCE: 123
tcttagcctt gccagcagat         20

<210> SEQ ID NO 124
<211> LENGTH: 20
<212> TYPE: DNA
<213> ORGANISM: Homo sapiens

<400> SEQUENCE: 124
cctttccagc tgtccctaga         20

<210> SEQ ID NO 125
<211> LENGTH: 20
<212> TYPE: DNA
<213> ORGANISM: Homo sapiens

<400> SEQUENCE: 125
aggatggcca attctcacag         20

<210> SEQ ID NO 126
<211> LENGTH: 20
<212> TYPE: DNA
<213> ORGANISM: Homo sapiens

<400> SEQUENCE: 126
aatgaatgcc agtggtcaca         20

<210> SEQ ID NO 127
<211> LENGTH: 20
<212> TYPE: DNA
<213> ORGANISM: Homo sapiens

<400> SEQUENCE: 127
tcttgtcaat gatgggtgga         20

<210> SEQ ID NO 128
<211> LENGTH: 19
<212> TYPE: DNA
<213> ORGANISM: Homo sapiens

<400> SEQUENCE: 128
ctccaggggg atccttgta         19

<210> SEQ ID NO 129
<211> LENGTH: 20
<212> TYPE: DNA
<213> ORGANISM: Homo sapiens

<400> SEQUENCE: 129
gtgcgcacct cggtattaac         20

<210> SEQ ID NO 130
<211> LENGTH: 20
<212> TYPE: DNA
<213> ORGANISM: Homo sapiens

<400> SEQUENCE: 130
tgaacagacc tcgcagacac         20

<210> SEQ ID NO 131
<211> LENGTH: 20

```
<212> TYPE: DNA
<213> ORGANISM: Homo sapiens

<400> SEQUENCE: 131
agcaacttgc aggaacgaat                                                   20

<210> SEQ ID NO 132
<211> LENGTH: 20
<212> TYPE: DNA
<213> ORGANISM: Homo sapiens

<400> SEQUENCE: 132
acgccttttc agatcacacc                                                   20

<210> SEQ ID NO 133
<211> LENGTH: 19
<212> TYPE: DNA
<213> ORGANISM: Homo sapiens

<400> SEQUENCE: 133
ggcaagggat ccaattctg                                                    19

<210> SEQ ID NO 134
<211> LENGTH: 20
<212> TYPE: DNA
<213> ORGANISM: Homo sapiens

<400> SEQUENCE: 134
cacaatggta cgcacctgac                                                   20

<210> SEQ ID NO 135
<211> LENGTH: 20
<212> TYPE: DNA
<213> ORGANISM: Homo sapiens

<400> SEQUENCE: 135
ccttcgcttg gtctagttcg                                                   20

<210> SEQ ID NO 136
<211> LENGTH: 20
<212> TYPE: DNA
<213> ORGANISM: Homo sapiens

<400> SEQUENCE: 136
tttcatgcct cgaggagact                                                   20

<210> SEQ ID NO 137
<211> LENGTH: 20
<212> TYPE: DNA
<213> ORGANISM: Homo sapiens

<400> SEQUENCE: 137
gagaagccta agacgcagga                                                   20

<210> SEQ ID NO 138
<211> LENGTH: 20
<212> TYPE: DNA
<213> ORGANISM: Homo sapiens

<400> SEQUENCE: 138
atactgggca accaggtcac                                                   20

<210> SEQ ID NO 139
```

```
<211> LENGTH: 20
<212> TYPE: DNA
<213> ORGANISM: Homo sapiens

<400> SEQUENCE: 139
gggcacggtg tccttaaata                                                 20

<210> SEQ ID NO 140
<211> LENGTH: 20
<212> TYPE: DNA
<213> ORGANISM: Homo sapiens

<400> SEQUENCE: 140
ctgggtgctt caaggatgag                                                 20

<210> SEQ ID NO 141
<211> LENGTH: 20
<212> TYPE: DNA
<213> ORGANISM: Homo sapiens

<400> SEQUENCE: 141
agcctccttg tccttgtcct                                                 20

<210> SEQ ID NO 142
<211> LENGTH: 20
<212> TYPE: DNA
<213> ORGANISM: Homo sapiens

<400> SEQUENCE: 142
ccttctggat ccttggattg                                                 20

<210> SEQ ID NO 143
<211> LENGTH: 20
<212> TYPE: DNA
<213> ORGANISM: Homo sapiens

<400> SEQUENCE: 143
ttggactgga tagggagcac                                                 20

<210> SEQ ID NO 144
<211> LENGTH: 20
<212> TYPE: DNA
<213> ORGANISM: Homo sapiens

<400> SEQUENCE: 144 cctttcccctt tcctcgaact                                                20

<210> SEQ ID NO 145
<211> LENGTH: 20
<212> TYPE: DNA
<213> ORGANISM: Homo sapiens

<400> SEQUENCE: 145
gcacatgctg aagatcatgc                                                 20

<210> SEQ ID NO 146
<211> LENGTH: 20
<212> TYPE: DNA
<213> ORGANISM: Homo sapiens

<400> SEQUENCE: 146
cctggtcact ccaagtccat                                                 20
```

```
<210> SEQ ID NO 147
<211> LENGTH: 20
<212> TYPE: DNA
<213> ORGANISM: Homo sapiens

<400> SEQUENCE: 147
gcggttcatt ttctttccaa                                              20

<210> SEQ ID NO 148
<211> LENGTH: 20
<212> TYPE: DNA
<213> ORGANISM: Homo sapiens

<400> SEQUENCE: 148
ttgattcctt tcccacaagc                                              20

<210> SEQ ID NO 149
<211> LENGTH: 20
<212> TYPE: DNA
<213> ORGANISM: Homo sapiens

<400> SEQUENCE: 149
acggtaccat gtcccatcat                                              20

<210> SEQ ID NO 150
<211> LENGTH: 20
<212> TYPE: DNA
<213> ORGANISM: Homo sapiens

<400> SEQUENCE: 150
ttctgtcacc cccttgagtc                                              20

<210> SEQ ID NO 151
<211> LENGTH: 20
<212> TYPE: DNA
<213> ORGANISM: Homo sapiens

<400> SEQUENCE: 151
gcccagcagg ttcatgtagt                                              20

<210> SEQ ID NO 152
<211> LENGTH: 20
<212> TYPE: DNA
<213> ORGANISM: Homo sapiens

<400> SEQUENCE: 152
ccacccaaac atctcaaacc                                              20

<210> SEQ ID NO 153
<211> LENGTH: 20
<212> TYPE: DNA
<213> ORGANISM: Homo sapiens

<400> SEQUENCE: 153
tcccatacgc ctacttctgc                                              20

<210> SEQ ID NO 154
<211> LENGTH: 20
<212> TYPE: DNA
<213> ORGANISM: Homo sapiens

<400> SEQUENCE: 154
ctgggaggga tgagattgaa                                              20
```

```
<210> SEQ ID NO 155
<211> LENGTH: 20
<212> TYPE: DNA
<213> ORGANISM: Homo sapiens

<400> SEQUENCE: 155
tctatggctt gctctggtga                                               20

<210> SEQ ID NO 156
<211> LENGTH: 20
<212> TYPE: DNA
<213> ORGANISM: Homo sapiens

<400> SEQUENCE: 156
gcattgggta tccatccatc                                               20

<210> SEQ ID NO 157
<211> LENGTH: 20
<212> TYPE: DNA
<213> ORGANISM: Homo sapiens

<400> SEQUENCE: 157
gggcttccct aagcacaaat                                               20

<210> SEQ ID NO 158
<211> LENGTH: 21
<212> TYPE: DNA
<213> ORGANISM: Homo sapiens

<400> SEQUENCE: 158
ccgtttcctt actgacctgc t                                             21

<210> SEQ ID NO 159
<211> LENGTH: 20
<212> TYPE: DNA
<213> ORGANISM: Homo sapiens

<400> SEQUENCE: 159
actttgggag gctgagacag                                               20

<210> SEQ ID NO 160
<211> LENGTH: 21
<212> TYPE: DNA
<213> ORGANISM: Homo sapiens

<400> SEQUENCE: 160
ttgccattct gtacacctga a                                             21

<210> SEQ ID NO 161
<211> LENGTH: 20
<212> TYPE: DNA
<213> ORGANISM: Homo sapiens

<400> SEQUENCE: 161
cgaaggcacg tttccttaga                                               20

<210> SEQ ID NO 162
<211> LENGTH: 20
<212> TYPE: DNA
<213> ORGANISM: Homo sapiens

<400> SEQUENCE: 162
gggctcacaa gacaggaaga                                               20
```

<210> SEQ ID NO 163
<211> LENGTH: 20
<212> TYPE: DNA
<213> ORGANISM: Homo sapiens

<400> SEQUENCE: 163
cctcttactc cccctcacct                                               20

<210> SEQ ID NO 164
<211> LENGTH: 20
<212> TYPE: DNA
<213> ORGANISM: Homo sapiens

<400> SEQUENCE: 164
gccagggtca gtgattcttc                                               20

<210> SEQ ID NO 165
<211> LENGTH: 20
<212> TYPE: DNA
<213> ORGANISM: Homo sapiens

<400> SEQUENCE: 165
ggaaggctgt gggtctcata                                               20

<210> SEQ ID NO 166
<211> LENGTH: 19
<212> TYPE: DNA
<213> ORGANISM: Homo sapiens

<400> SEQUENCE: 166
caggcctttg tcctgatcc                                                19

<210> SEQ ID NO 167
<211> LENGTH: 20
<212> TYPE: DNA
<213> ORGANISM: Homo sapiens

<400> SEQUENCE: 167
ccacatgctg gcatctctac                                               20

<210> SEQ ID NO 168
<211> LENGTH: 20
<212> TYPE: DNA
<213> ORGANISM: Homo sapiens

<400> SEQUENCE: 168
cctcacagaa cttggccttc                                               20

<210> SEQ ID NO 169
<211> LENGTH: 20
<212> TYPE: DNA
<213> ORGANISM: Homo sapiens

<400> SEQUENCE: 169
gggacacgac ctgagaagtc                                               20

<210> SEQ ID NO 170
<211> LENGTH: 20
<212> TYPE: DNA
<213> ORGANISM: Homo sapiens

<400> SEQUENCE: 170

```
tcacaggtac cgttggttga                                           20
```

<210> SEQ ID NO 171
<211> LENGTH: 20
<212> TYPE: DNA
<213> ORGANISM: Homo sapiens

<400> SEQUENCE: 171

```
agggccgagt tttgtttgtt                                           20
```

<210> SEQ ID NO 172
<211> LENGTH: 22
<212> TYPE: DNA
<213> ORGANISM: Homo sapiens

<400> SEQUENCE: 172

```
ggaattacaa ggaagtgcca at                                        22
```

<210> SEQ ID NO 173
<211> LENGTH: 20
<212> TYPE: DNA
<213> ORGANISM: Homo sapiens

<400> SEQUENCE: 173

```
aaagggccct gacaactctt                                           20
```

<210> SEQ ID NO 174
<211> LENGTH: 20
<212> TYPE: DNA
<213> ORGANISM: Homo sapiens

<400> SEQUENCE: 174

```
ttaggcggag tcttgaggaa                                           20
```

<210> SEQ ID NO 175
<211> LENGTH: 21
<212> TYPE: DNA
<213> ORGANISM: Homo sapiens

<400> SEQUENCE: 175

```
ccaacaggat acctgaagca a                                         21
```

<210> SEQ ID NO 176
<211> LENGTH: 20
<212> TYPE: DNA
<213> ORGANISM: Homo sapiens

<400> SEQUENCE: 176

```
cctcctgagc agctgagatt                                           20
```

<210> SEQ ID NO 177
<211> LENGTH: 20
<212> TYPE: DNA
<213> ORGANISM: Homo sapiens

<400> SEQUENCE: 177

```
gacaattggc aaaattggaa                                           20
```

<210> SEQ ID NO 178
<211> LENGTH: 20
<212> TYPE: DNA
<213> ORGANISM: Homo sapiens

<400> SEQUENCE: 178
aagctccctg aggacagaca                                              20

<210> SEQ ID NO 179
<211> LENGTH: 20
<212> TYPE: DNA
<213> ORGANISM: Homo sapiens

<400> SEQUENCE: 179
ctccagttcc cagcaagttc                                              20

<210> SEQ ID NO 180
<211> LENGTH: 20
<212> TYPE: DNA
<213> ORGANISM: Homo sapiens

<400> SEQUENCE: 180
tggtggcttc tgagtgttca                                              20

<210> SEQ ID NO 181
<211> LENGTH: 20
<212> TYPE: DNA
<213> ORGANISM: Homo sapiens

<400> SEQUENCE: 181
ggtcacccat tctagcctca                                              20

<210> SEQ ID NO 182
<211> LENGTH: 20
<212> TYPE: DNA
<213> ORGANISM: Homo sapiens

<400> SEQUENCE: 182
cttgaggagc acctgtcaga                                              20

<210> SEQ ID NO 183
<211> LENGTH: 18
<212> TYPE: DNA
<213> ORGANISM: Homo sapiens

<400> SEQUENCE: 183
gccctgggga gctacaag                                                18

<210> SEQ ID NO 184
<211> LENGTH: 20
<212> TYPE: DNA
<213> ORGANISM: Homo sapiens

<400> SEQUENCE: 184
gtgagccagg catcctacat                                              20

<210> SEQ ID NO 185
<211> LENGTH: 20
<212> TYPE: DNA
<213> ORGANISM: Homo sapiens

<400> SEQUENCE: 185
gcctctctac cctccctcag                                              20

<210> SEQ ID NO 186
<211> LENGTH: 20
<212> TYPE: DNA
<213> ORGANISM: Homo sapiens

```
<400> SEQUENCE: 186
aatatttgtg cggggtatgg                                                    20

<210> SEQ ID NO 187
<211> LENGTH: 20
<212> TYPE: DNA
<213> ORGANISM: Homo sapiens

<400> SEQUENCE: 187
aagtgggacg aacacctgtc                                                    20

<210> SEQ ID NO 188
<211> LENGTH: 20
<212> TYPE: DNA
<213> ORGANISM: Homo sapiens

<400> SEQUENCE: 188
tttaggacac accccaccat                                                    20

<210> SEQ ID NO 189
<211> LENGTH: 20
<212> TYPE: DNA
<213> ORGANISM: Homo sapiens

<400> SEQUENCE: 189
atcgaccaca gaaggcattt                                                    20

<210> SEQ ID NO 190
<211> LENGTH: 20
<212> TYPE: DNA
<213> ORGANISM: Homo sapiens

<400> SEQUENCE: 190
ggtggtccag gggtcttact                                                    20
```

PHOSPHATASE ASSOCIATED WITH METASTASIS

This application claims the benefit of provisional application 60/327,332 filed Oct. 9, 2001, the disclosure of which is expressly incorporated herein, and is a continuation of international application PCT/US02/31247, filed Oct. 2, 2002.

This invention was made with support from NIH grants CA57345 and CA43460. The U.S. government therefore retains certain rights in the invention.

BACKGROUND OF THE INVENTION

1. Field of the Invention

The invention relates to the field of cancer diagnostics and therapeutics. In particular it relates to a gene which appears to be significantly associated with the progression of cancer to more advanced stages, including metastasis.

2. Background of the Prior Art

Metastasis is the neoplastic process responsible for most deaths from cancer, as the primary tumors can usually be surgically removed. Metastatic cells cytoskeletal changes, loss of adhesion, enhanced motility, and express proteolytic enzymes that degrade the basement membrane (1-3). However, much remains to be learned about this lethal process and further progress is contingent upon identifying novel genes and pathways that are consistently and specifically altered in metastatic lesions.

In the case of colorectal tumorigenesis, the genes associated with initiation and progression to the invasive (cancerous) stage are well known (4). However, no gene has been shown to be consistently and specifically activated in liver metastases, the lesions that are usually responsible for the death of colorectal cancer patients. There is a continuing need in the art for targets which are consistently and specifically activated in metastatic cancers.

BRIEF SUMMARY OF THE INVENTION

In a first embodiment the invention provides a method of identifying regions of neoplastic growth in a human body. An antibody which specifically binds to a protein marker of neoplastic growth is administered to the human body. The protein marker is selected from the group consisting of protein tyrosine phosphatase type IVA, member 3, FLJ23603, LOC54675, ZD52F10, DNAJ domain-containing, GRO3 oncogene/T45117 hU1-70K protein, attractin, Bc1-2 binding component 3, nuclear receptor subfamily 4, mitogen activated protein kinase 8 interacting protein 2, hairy (Drosophila)-homolog, LUC7 (S. cerevesiae)-like, transducin-like enhancer of split 2, homolog of Drosophila E (sp1), adipose differentiation-related protein, keratin 17, casein kinase 2, alpha prime polypeptide, minichromosome maintenance deficient (S. cerevisiae) 7, v-jun avian sarcoma virus 17 oncogene homolog/LSFR2 gene 2/MGC2550 protein, plexin B1, transforming growth factor, beta 1ESTs, similar to GTP-rho binding protein 1 (rhophilin), (Drosophila)-like homeo box 1mago-nashi (Drosophila) homolog, proliferation-associated, putative Rab5-interacting protein vascular endothelial growth factor, PTD008 protein, protein/ribosomal protein L10, wee1+(S. pombe) homolog/proteinx013, cDNA: FLJ12683, PTK7 protein tyrosine kinase 7v-fos FBJ murine osteosarcoma viral oncogene homolog B, FLJ20297 protein SET translocation (myeloid leukemia-associated), chaperonin containing TCP1, subunit 6A (zeta 1), ataxin 2 related protein, cyclin-dependent kinase inhibitor 3 (CDK2-associated dual specificity phosphatase), and matrix metalloproteinase 14 (membrane-inserted). Regions of the human body to which the antibody has specifically bound are detected.

According to another embodiment of the invention a method is provided to aid in the prediction of metastasis. Amplification of a first chromosomal segment encoding protein tyrosine phosphatase type IVA, member 3, is detected in a tissue sample of a human. A hybridization probe which hybridizes to all or a portion of a gene encoding protein tyrosine phosphatase type IVA member 3 or primers which amplify all or a portion of protein tyrosine phosphatase type IVA is used to detect the amplification. Detection of such amplification suggests propensity of the tissue to metastasize.

Still another embodiment of the invention is a method to aid in the prediction of metastasis. Excess expression in a tissue sample of a human of a gene is detected. The gene is selected from the group consisting of protein tyrosine phosphatase type IVA member 3, FLJ23603, LOC54675, ZD52F10, DNAJ domain-containing, GRO3 oncogene/T45117 hU1-70K protein, attractin, Bc1-2 binding component 3, nuclear receptor subfamily 4, mitogen activated protein kinase 8 interacting protein 2, hairy (Drosophila)-homolog, LUC7 (S. cerevesiae)-like, transducin-like enhancer of split 2, homolog of Drosophila E (sp1), adipose differentiation-related protein, keratin 17, casein kinase 2, alpha prime polypeptide, minichromosome maintenance deficient (S. cerevisiae) 7, v-jun avian sarcoma virus 17 oncogene homolog/LSFR2 gene 2/MGC2550 protein, plexin B1, transforming growth factor, beta 1ESTs, similar to GTP-rho binding protein 1 (rhophilin), (Drosophila)-like homeo box Imago-nashi (Drosophila) homolog, proliferation-associated, putative Rab5-interacting protein vascular endothelial growth factor, PTD008 protein, protein/ribosomal protein L10, wee1+ (S. pombe) homolog/proteinx013, cDNA: FLJ12683, PTK7 protein tyrosine kinase 7v-fos FBJ murine osteosarcoma viral oncogene homolog B, FLJ20297 protein SET translocation (myeloid leukemia-associated), chaperonin containing TCP1, subunit 6A (zeta 1), ataxin 2 related protein, cyclin-dependent kinase inhibitor 3 (CDK2-associated dual specificity phosphatase), and matrix metalloproteinase 14 (membrane-inserted). Excess expression is determined when elevated expression in the tissue sample relative to a non-pathological sample of the human is observed. Observation of excess expression indicates that the tissue sample has a propensity to metastasize relative to the non-pathological sample.

Also provided by the present invention is an embodiment which can be used as an aid in the prediction of metastasis. Excess expression of a gene is detected in a stool specimen of a human patient having a gastrointestinal neoplasm. The gene is selected from the group consisting of protein tyrosine phosphatase type IVA member 3, FLJ23603, LOC54675, ZD52F10, DNAJ domain-containing, GRO3 oncogene/T45117 hU1-70K protein, attractin, Bc1-2 binding component 3, nuclear receptor subfamily 4, mitogen activated protein kinase 8 interacting protein 2, hairy (Drosophila)-homolog, LUC7 (S. cerevesiae)-like, transducin-like enhancer of split 2, homolog of Drosophila E (sp1), adipose differentiation-related protein, keratin 17, casein kinase 2, alpha prime polypeptide, minichromosome maintenance deficient (S. cerevisiae) 7, v-jun avian sarcoma virus 17 oncogene homolog/LSFR2 gene 2/MGC2550 protein, plexin B1, transforming growth factor, beta 1ESTs, similar to GTP-rho binding protein 1 (rhophilin), (Drosophila)-like homeo box 1mago-nashi (Drosophila) homolog, proliferation-associated, putative Rab5-interacting protein vascular endothelial growth factor, PTD008 protein, protein/ribosomal protein L10, wee1+ (S. pombe) homolog/proteinx013, cDNA:

FLJ12683, PTK7 protein tyrosine kinase 7v-fos FBJ murine osteosarcoma viral oncogene homolog B, FLJ20297 protein SET translocation (myeloid leukemia-associated), chaperonin containing TCP1, subunit 6A (zeta 1), ataxin 2 related protein, cyclin-dependent kinase inhibitor 3 (CDK2-associated dual specificity phosphatase), and matrix metalloproteinase 14 (membrane-inserted). Excess expression is elevated expression in the stool specimen relative to a stool specimen of a human who does not have a gastrointestinal neoplasm. Excess expression permits the identification of the human patient as having a metastasis or a propensity for a cancer to metastasize.

Another aspect of the invention is a method of treating a patient with an advanced or metastatic cancer. An antibody is administered to the patient. The antibody specifically binds to a protein encoded by a gene selected from the group consisting of protein tyrosine phosphatase type IVA member 3, FLJ23603, LOC54675, ZD52F10, DNAJ domain-containing, GRO3 oncogene1T45117 hU1-70K protein, attractin, Bcl-2 binding component 3, nuclear receptor subfamily 4, mitogen activated protein kinase 8 interacting protein 2, hairy (Drosophila)-homolog, LUC7 (S. cerevesiae)-like, transducin-like enhancer of split 2, homolog of Drosophila E (sp1), adipose differentiation-related protein, keratin 17, casein kinase 2, alpha prime polypeptide, minichromosome maintenance deficient (S. cerevisiae) 7, v-jun avian sarcoma virus 17 oncogene homolog/LSFR2 gene 2/MGC2550 protein, plexin B1, transforming growth factor, beta 1ESTs, similar to GTP-rho binding protein 1 (rhophilin), (Drosophila)-like homeo box 1mago-nashi (Drosophila) homolog, proliferation-associated, putative Rab5-interacting protein vascular endothelial growth factor, PTD008 protein, protein/ribosomal protein L10, weel+ (S. pombe) homolog/proteinx013, cDNA: FLJ12683, PTK7 protein tyrosine kinase 7v-fos FBJ murine osteosarcoma viral oncogene homolog B, FLJ20297 protein SET translocation (myeloid leukemia-associated), chaperonin containing TCP1, subunit 6A (zeta 1), ataxin 2 related protein, cyclin-dependent kinase inhibitor 3 (CDK2-associated dual specificity phosphatase), and matrix metalloproteinase 14 (membrane-inserted). Growth of the cancer is thereby inhibited.

According to another aspect of the invention a method of treating a patient having advanced or metastatic gastrointestinal cancer is provided. An inhibitor of protein tyrosine phosphatase type IVA member 3 is administered to the patient.

Yet another aspect of the invention provides a method to identify candidate drugs useful for treating advanced or metastatic tumors. The relative ability of a test compound to inhibit PRL-3 activity, relative to an enzyme selected from the group consisting of PRL-2 and PRL-1 is determined. A test compound which specifically inhibits PRL-3 activity preferentially relative to either PRL-2 or PRL-1 is identified as a compound potentially useful in treating advanced or metastatic tumors.

BRIEF DESCRIPTION OF THE DRAWINGS

(FIG. 2A) Gel of RT-PCR products from normal colorectal epithelium (N1 to N3), adenomas (A1 to A3), primary cancers (C1 to C3), and metastases (M1 to M3). Real-time PCR was performed for 24 cycles, when RT-PCR products from the metastases were evident but before signals from the other lesions had appeared. Arrow indicates the PRL-3 RT-PCR product of 198 bp. (FIG. 2B) Results are expressed as the ratio between PRL-3 and APP expression, and are normalized to the average expression in adenomas. Duplicates are shown for each analysis.

(FIG. 3B) Relative levels of expression were determined as in FIG. 2.

DETAILED DESCRIPTION OF THE INVENTION

Figure 1:
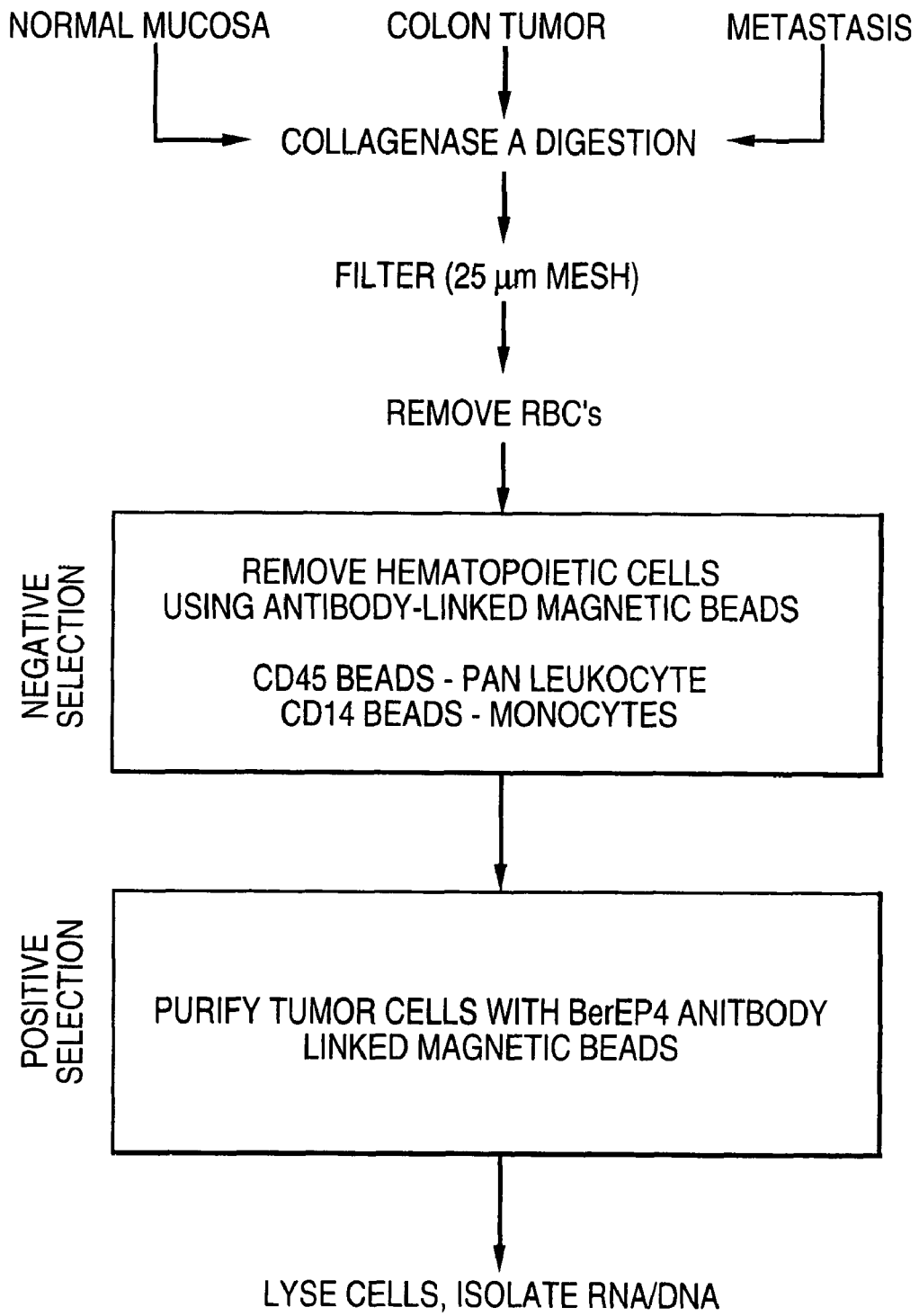
FIG. 1. Purification of epithelial cells. Colonic epithelial cells were purified using modifications of a previously described immunoaffinity purification scheme for purifying endothelial cells (St Croix et al., Science 289, 1197 (2000)). Tissues were obtained immediately after surgical removal and digested with collagenase for 1 hour at 37C. A single cell suspension was obtained after a series of sequential filterings through nylon mesh of 400 m, 50 m, and 25 m. A cocktail of anti-CD14 and anti-CD45 immunomagnetic beads (Dynal) was used to remove hematopoietic cells as well as cells binding non-specifically to the magnetic beads (negative selection). Subsequently, the epithelial cells remaining in the cell suspension were isolated by binding to anti-BerEP4 immunomagnetic beads (Dynal) (positive selection). The BerEP4 antibody recognizes a pan-epithelial antigen present on normal and neoplastic colonic epithelium but not present on hepatocytes or stromal cells (U. Latza, G. Niedobitek, R. Schwarting, H. Nekarda, H. Stein, J. Clin. Pathol. 43, 213 (1990)). The BerEP4 bound epithelial cells were quantified with a hemocytometer.

It is a discovery of the inventors that a set of genes are specifically expressed to a higher level in metastatic cancers than in advanced cancers and than in early stage cancers and than in normal cells from which they derive. Such genes are identified in Table 1 (with their SAGE tags shown as SEQ ID NO: 5-42, respectively). One gene appears to be particularly useful, a tyrosine phosphatase (protein tyrosine phosphatase type IVA member 3, also known as PRL-3) that is consistently overexpressed in metastatic colorectal cancers. The genes of Table 1 represent excellent targets for diagnostic and therapeutic use, as well as targets for drug screening programs.

One way in which the targets identified in the present invention can be used is for diagnostic imaging. Antibodies can be used to specifically target an imaging agent (detectable label) to the locations of the body in which metastases have infiltrated. Antibodies which specifically bind to one of the targets and do not appreciably or detectably bind to other proteins or components of the human body are preferred. Less preferred are antibodies which bind preferentially to an identified target relative to other components of the human body. Antibodies can be polyclonal or monoclonal, full molecules or fragments. Many fragments of antibodies are typically used which retain binding activity of the full antibodies. Such antibody fragments include but are not limited to Fab, Fab2, Fab', Fab'2, and Single chain Fv (scFv). The antibodies or fragments thereof (collectively referred to as antibodies) can be combined, conjugated, attached, coupled, or otherwise linked to a detectable label. The linkage to the detectable label can be covalent or noncovalent; strong linkages are preferred. The detectable labels can be directly linked to the antibody specific for the target or it can be coupled via a second moiety, such as via a second antibody specific for the first antibody or via a biotin/avidin or biotin/strepavidin type linkage. The detectable label can be delivered at the same time as the antibody specific for the target or subsequently. Such detectable labels include radioisotopes, fluorescent moieties, enzymatic labels, and the like. Any label which is readily detectable using non-invasive techniques is preferred, although endoscopy can also be used to identify areas of localization of the detectable label.

Similarly, peptides can be used to bind specfically to one of the identified targets. Peptides can be identified by screening of peptide expression libraries; phage display libraries are particularly preferred. Combinatorial peptide libraries can also be screened. Such peptides can be labeled in the same fashion as antibodies for detection in a human body. Non-peptide agents, such as small organic molecules can also be used. These can be the results of combinatorial chemistry or other techniques or aggregates of techniques which lead to large numbers of diverse molecules. In some cases lead compounds can be used as the basis for the combinatorial library development. In other cases the library will be randomly made.

Methods for the synthesis of molecular libraries are well known in the art (see, for example, DeWitt et al., *Proc. Natl. Acad. Sci. U.S.A.* 90, 6909, 1993; Erb et al. *Proc. Natl. Acad. Sci. U.S.A.* 91, 11422, 1994; Zuckermann et al., *J. Med. Chem.* 37, 2678, 1994; Cho et al., *Science* 261, 1303, 1993; Carell et al., *Angew. Chem. Int. Ed. Engl.* 33, 2059, 1994; Carell et al., *Angew. Chem. Int. Ed. Engl.* 33, 2061; Gallop et al., *J. Med. Chem.* 37, 1233, 1994). Libraries of compounds can be presented in solution (see, e.g., Houghten, *BioTechniques* 13, 412-421, 1992), or on beads (Lam, *Nature* 354, 82-84, 1991), chips (Fodor, *Nature* 364, 555-556, 1993), bacteria or spores (Ladner, U.S. Pat. No. 5,223,409), plasmids (Cull et al., *Proc. Natl. Acad. Sci. U.S.A.* 89, 1865-1869, 1992), or phage (Scott & Smith, *Science* 249, 386-390, 1990; Devlin, *Science* 249, 404-406, 1990); Cwirla et al., *Proc. Natl. Acad. Sci.* 97, 6378-6382, 1990; Felici, *J. Mol. Biol.* 222, 301-310, 1991; and Ladner, U.S. Pat. No. 5,223,409).

A human target polypeptide can alternatively be used as a "bait protein" in a two-hybrid assay or three-hybrid assay (see, e.g., U.S. Pat. No. 5,283,317; Zervos et al., *Cell* 72, 223-232, 1993; Madura et al., *J. Biol. Chem.* 268, 12046-12054, 1993; Bartel et al., *BioTechniques* 14, 920-924, 1993; Iwabuchi et al., *Oncogene* 8, 1693-1696, 1993; and Brent WO94/10300), to identify other proteins which bind to or interact with the target polypeptide and modulate its activity.

The two-hybrid system is based on the modular nature of most transcription factors, which consist of separable DNA-binding and activation domains. Briefly, the assay utilizes two different DNA constructs. For example, in one construct, polynucleotide encoding a human target polypeptide can be fused to a polynucleotide encoding the DNA binding domain of a known transcription factor (e.g., GAL-4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein that interacts with the target polypeptide.

Antibodies and antibody fragments specific for the identified targets can also be used in a therapeutic modality. Such antibodies can be cytolytic. Alternatively the antibodies can be attached to a cytotoxic agent or a chemotherapeutic agent or a toxin or a radionuclide. Suitable agents for attaching to antibodies include capecitabine, mitoxantrone, aflotoxin, doxorubicin, cyclophosphamide, 5-fluorouracil, irinotecan, mitomycin, paclitaxol, cisplatinum, Pseudomonas exotoxin, bungarotoxin, ricin toxin. Such agents can be covalently attached to the antibody or attached via a linker moiety which may itself involve a specific binding pair, including biotin/avidin, biotin/strepavidin, antibody/antigen. For such therapeutic purposes, peptides and other agents which specifically bind to one of the identified targets can also be attached to a cytotoxic agent or a chemotherapeutic agent.

Antibodies can be delivered to the patient by any means known in the art. Generally these include intravenous, intramuscular, subcutaneous, intratumoral injections or infusions. Antibodies are typically provided in an aqueous formulation designed to maintain structure and binding ability of the antibody and to be pharmaceutically acceptable to the patient. Desirably such formulations are sterile and pyrogen-free.

If the target is an enzyme, specific inhibitors of the enzyme can be used to inhibit the enzyme and thereby inhibit the growth of the tumor or cancer or progression of the metastatic process. In the case of protein tyrosine phosphatase type IVA member 3, compounds having a vanadate moiety are particularly useful. These include sodium orthovanadate, potassium bisperoxo (bipyridine) oxovanadate (V), bisperoxo vanadium (phenyl), bisperoxo vanadium (bipyridine), bisperoxo vanadium (ammonium cation), bisperoxo vanadium (picolinic acid dianion), bisperoxo vanadium (5-hydroxypyridine-2-carboxylic acid anion), and others as taught in Posner, "Peroxovanadium Compounds, a new class of potent phosphotyosine phosphatase inhibitors which are insulin mimetics," J. Biol. Chem. 269: 45964804, 1994. Such compounds can be administered by any effective means for the particular compound, including but not limited to intravenous, subcutaneous, intrathecal, intramuscular, and oral administration, as well as surgical implant of a slow release device. Other inhibitors as are identified for protein phosphotyrosinase phosphatase IVA can be used. Inhibitors of other enzymes which are listed in Table 1 can also be used, alone or in combination.

Specific inhibitors are believed to be preferable to nonspecific inhibitors because they will cause less side-effects. Thus inhibitors which are specific for PRL-3 relative to PRL-1 or PRL-2 are preferred. Such compounds can be identified by a screen against each of these enzymes. Similarly, inhibitors which are specific for PRL-3 relative to other phosphatases or other enzymes are preferred. Test compounds which preferentially inhibit PRL-3 are identified. Standard enzyme assays can be used, or high throughput assays can be established. Substrates which can be used for testing PRL-3 activity include DiFMuP (6,8-difluoro-4-methylumbelliferyl phosphate), histone 2B, and p130$^{cas}$. The assays can utilize fluorescent substrates (like DiFMuP) or substrates having a radiolabled phosphotyrosine, for example, which is easily detectable upon release from the substrate. See Posner, supra, and Matter (13), the disclosures of which are expressly incorporated herein. Promising candidates can be subsequently tested for growth inhibitory activity against cancer cells in vitro and tumors in experimental animals.

Interestingly, some metastatic tumors carry an amplified segment of the genome at 8q24.3. The segment can be amplified at least 10, 15, 20, 25, or 30-fold over the level of other portions of chromosome 8q which are not amplified. The gene for tyrosine phosphatase type IVA is contained within the amplicon. The amplification explains the overexpression of the gene in at least some metastases. The presence of the amplified segment in a tissue sample can suggest that the tissue has a propensity to metastasize. When testing for the amplified segment, it is desirable to normalize the results against a second segment of chromosome 8q to insure that any increases observed in copy number of the 8q24.3 segment is not due to aneuploidy, which is frequently found in tumor cells. Copy number of gene segments can be determined using any technique known in the art, including hybridization to a nucleic acid probe or amplification with primers. Amplification of the 8q region has been observed in prostate, breast, and colorectal cancers. Thus this assay can be used to detect propensity to metastasize in any of such neoplastic tissues Another way to predict or determine the propensity to metastasize is to determine expression in a tissue sample of any of the genes of Table 1. Elevated expression of one or more of such genes is indicative of a propensity to metastasize. Determination of elevated expression is typically done by comparing to amount of expression in a non-pathological tissue sample of the human. Preferably the type of cells in the non-pathological tissue sample is the same or nearly the same as the type of cells in the tissue sample of the tumor being tested. Elevated expression is typically a level of at least 2, 5, or 10-fold increased relative to the level in the non-pathological control tissue. Any convenient method for determining expression levels, at either the protein or RNA level can be used. These include but are not limited to RT-PCR, real time PCR, hybridization to a nucleic acid array, immunoblotting, enzyme-linked immunoassay, other immunological assays, and enzyme activity assays.

Stool samples are often used to test for gastrointestinal cancers. The targets identified in the present invention can also be identified in stool samples. Excess expression of either the RNA or protein can often be reflected in the amounts of the RNA or protein found in the stool. Thus detection of the amount of the target's expression product in the stool, and comparison to the level in a stool specimen from one or more humans who do not have a gastrointestinal neoplasm can be used to detect metastasis or to predict the propensity to metastasize. Elevated expression can be determined when a level is found that is at least 2, 5, or 10-fold higher. Any of the methods for measuring expression products which are discussed above can be used for this purpose as well.

The fact that the PRL-3 gene is contained in a small amplicon in a subset of these tumors provides important, complementary evidence for the role of this gene in metastasis; the major genes previously shown to be amplified in naturally occurring cancers are all oncogenes (18, 23, 24). Extra copies of chromosome 8q DNA sequences have been observed in the advanced stages of many different tumor types, including advanced colon cancers (25-28). It has been suggested that the c-MYC gene on chromosome 8q24.12 is the target of such 8q over-representation. In the three metastatic lesions we examined, c-MYC was not amplified and was in fact ~14 Mb from the boundaries of the PRL-3 amplicon.

One of the most important ramifications of the work described here concerns its potential therapeutic implications. Most of the previously described genetic alterations in colorectal cancers involve inactivation of tumor suppressor genes. The proteins produced from these genes are difficult to target with drugs, as they are inactive or absent in the cancer cells (29). In contrast, enzymes whose expression is elevated in cancer cells, like that encoded by PRL-3, provide excellent targets for drug discovery purposes.

EXAMPLES

Example 1

SAGE Analysis of Liver Metastases

To learn which genes might be involved in this process, we performed global gene expression profiles of liver metastases using Serial Analysis of Gene Expression (SAGE) technology (5). We first prepared a SAGE library from microdissected metastases (6). Surprisingly, we found that many of the transcripts identified in these libraries were characteristic of normal hepatic or inflammatory cells, precluding quantitative analysis (7). To produce a more specific profile of metastatic epithelial cells, we developed an immunoaffinity fractionation procedure to purify colorectal epithelial cells from contaminating stromal and hepatic cells (8). A SAGE library was prepared from cells purified in this manner, yielding ~95,000 tags representing at least 17,324 transcripts (6). These tags were compared to ~4 million tags derived from diverse SAGE libraries, particularly those from normal and malignant (but non-metastatic) colorectal epithelium (9). One hundred forty-four transcripts were represented at significantly higher levels in the metastasis library than in the other libraries, while 79 transcripts were represented at significantly lower levels in the metastasis library (10)

Purification of Colorectal Epithelial Cells.

Colonic epithelial cells were purified using modifications of a previously described immunoaffinity purification scheme for purifying endothelial cells (St Croix et al., Science 289, 1197 (2000)). Tissues were obtained immediately after surgical removal and digested with collagenase for 1 hour at 37° C. A single cell suspension was obtained after a series of sequential filterings through nylon mesh of 400 mm, 50 mm, and 25 mm. A cocktail of anti-CD14 and anti-CD45 immunomagnetic beads (Dynal) was used to remove hematopoietic cells as well as cells binding non-specifically to the magnetic beads (negative selection). Subsequently, the epithelial cells remaining in the cell suspension were isolated by binding to anti-BerEP4 immunomagnetic beads (Dynal) (positive selection). The BerEP4 antibody recognizes a pan-epithelial antigen present on normal and neoplastic colonic epithelium but not present on hepatocytes or stromal cells (U. Latza, G. Niedobitek, R. Schwarting, H. Nekarda, H. Stein, J. Clin. Pathol. 43, 213 (1990)). The BerEP4 bound epithelial cells were quantified with a hemocytometer.

Methods for Preparation and Analysis of RNA.

Total RNA was isolated using RNAgents (Promega, Madison, Wis.) and mRNA was selected using the MessageMaker Reagent Assembly (Gibco BRL). Single-stranded cDNA was generated using Superscript II Reverse Transcriptase (Gibco BRL) following the manufacturer's directions. Mock template preparations were prepared in parallel without the addition of reverse transcriptase. Quantitative PCR was performed with an iCycler (Bio-Rad, Hercules, Calif.) using Pico Green dye (Molecular Probes, Eugene, Oreg.), and threshold cycle numbers were obtained using iCycler software v2.3. Primer sets for each sequence analyzed are included in Table 2 (as SEQ ID NO: 81-118 (forward primers), SEQ ID NO: 119-156 (reverse primers), and SAGE tag for each sequence is SEQ ID NO: 43-80). Conditions for amplification were: one cycle of 95° C., 2 min followed by 35 cycles of 95° C., 15 sec, 58° C., 15 sec, and 72° C., 15 sec. Quantitative PCR reactions were performed in triplicate and threshold cycle numbers were averaged. RT-PCR products had to meet two criteria to be included in this study. First, the signal from the reverse transcriptase (RT)-derived cDNA had to be at least 100 fold greater than that of control reactions performed without reverse transcriptase. Second, the PCR products from the reactions with RT had to be the expected size upon gel electrophoresis. Gene expression was normalized to that of b-amyloid precursor protein (APP), a gene that is uniformly expressed in all colorectal tissues as assessed by SAGE. Relative expression was calculated using the formula $2(Rt-Et)/2(Rn-En)$ where Rt is the threshold cycle number observed in the experimental sample for APP, Et is the threshold cycle number observed in the experimental sample for PRL-3, Rn is the average threshold cycle number observed in six adenomas for APP and En is the average threshold cycle number observed in six adenomas for PRL-3.

Methods for Preparation and Analysis of DNA.

Genomic DNA was prepared from purified epithelial cells using the Qiagen DNA Easy Purification Kit (Qiagen). To assess gene copy number, we performed six independent replicates on each DNA sample. Real-time PCR was carried out as described above for the expression analysis, except that the control reactions were carried out without any genomic DNA template.

Primer 3 (Steve Rozen and Helen J. Skaletsky (2000) Primer3 on the WWW for general users and for biologist programmers. In: Krawetz S, Misener S (eds) *Bioinformatics Methods and Protocols: Methods in Molecular Biology*. Humana Press, Totowa, N.J., pp 365-386) was used to design primers for genomic PCR. Primer sets used for initial determination of copy numbers were CCTCACAGAACTTGGC-CTTC (SEQ ID NO: 1) and GCCTCTCTACCCTCCCTCAG (SEQ ID NO: 2) for PRL-3 and GGGCTTCCCTAAGCA-CAAAT (SEQ ID NO: 3) and TTAGGCGGAGTCTTGAG-GAA (SEQ ID NO: 4) for a proximal locus on chromosome 8q (Celera scaffold: GA_x5HB7VCY1B9). Conditions for amplification were: one cycle of 95° C., 2 min followed by 35 cycles of 95° C, 15 sec, 58° C, 15 sec, 72° C, 15 sec.

Example 2

Real-time PCR on Multiple Metastatic Lesions

Transcripts that were enriched rather than depleted in the metastasis library have obvious diagnostic and therapeutic potential. We therefore selected 38 of the most interesting enriched transcripts for further analysis (Table 1) (11). To confirm the SAGE data, we compared the expression of these transcripts in several microdissected metastases, primary cancers, pre-malignant adenomas, and normal epithelium by quantitative, real-time PCR (8). Though all 38 of these transcripts were found to be elevated in at least a subset of the metastatic lesions tested, only one gene, PRL-3, was found to be consistently overexpressed.

In Table 1, SAGE TAG refers to the 10 bp sequence immediately adjacent to the NlaIII restriction site (CATG) in each transcript. SAGE libraries were constructed from two normal colonic tissues (one library containing 48,479 tags, the other 49,610 tags), two primary colorectal cancers (one library containing 55,700 tags, the other 41,371 tags), and a colorectal metastasis (94,445 tags). Transcript description refers to the Unigene assignment of the SAGE TAG (National Center for Biotechnology Information). When tags matched two Unigene assignments, both are listed. The numbers listed in each column refer to the number of SAGE tags corresponding to the indicated gene that were observed in the library made from the indicated tissue. For example, 12 SAGE tags were observed for PRL-3 in the SAGE library from the metastasis, but no PRL-3 SAGE tags were observed in the other four libraries.

Example 3

Correlation of Expression of PRL-3 with Metastasis

Figure 2:
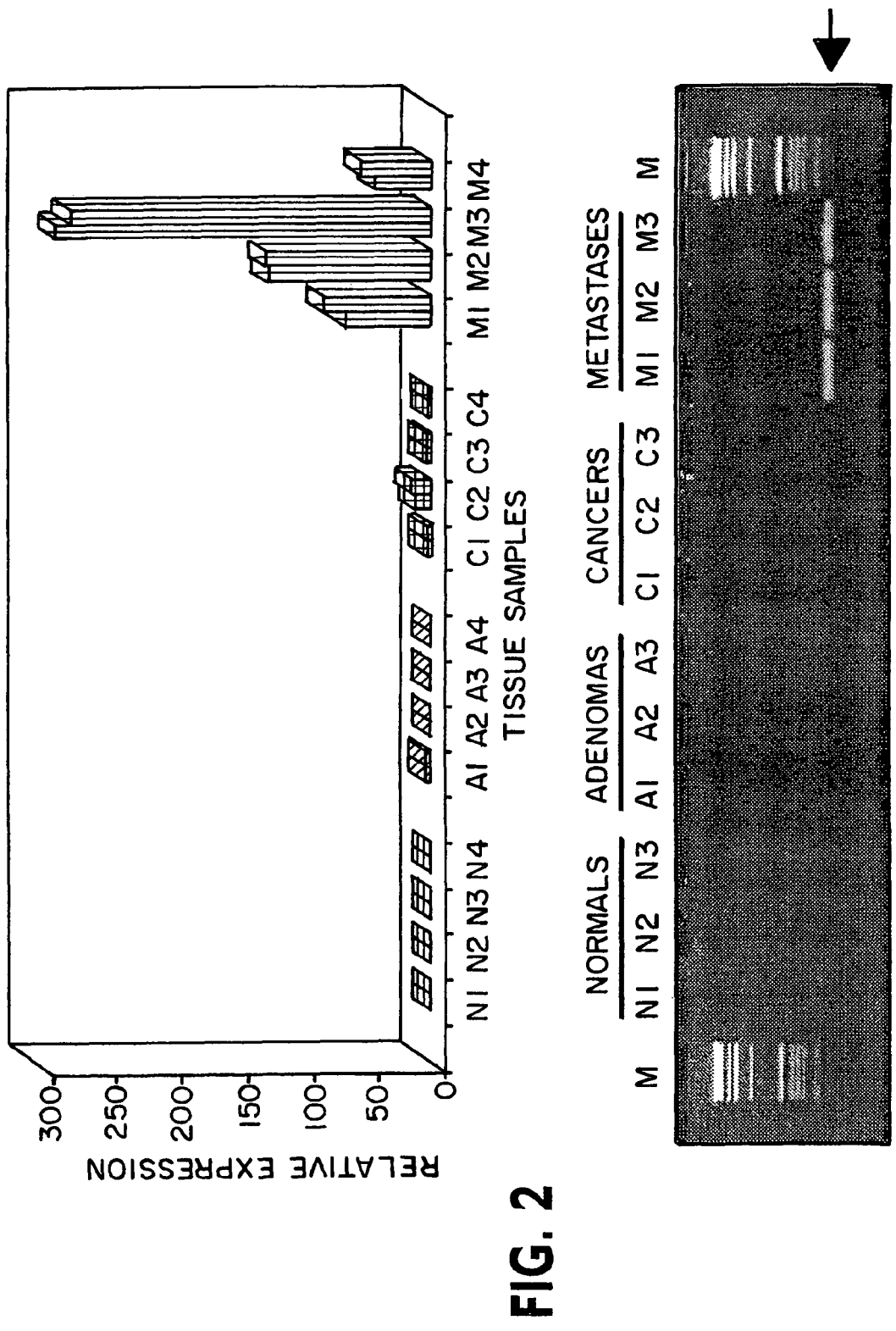
FIG. 2. PRL-3 expression in human colorectal tumors of different stage. The expression of PRL-3 was evaluated using real-time PCR (8) and compared to that of the β-amyloid precursor protein (APP) gene, shown previously to be expressed at nearly identical levels in normal and neoplastic colorectal tissues (9). The metastases analyzed in this experiment were derived from patients other than the ones from whom the normal epithelium and other lesions were derived. Epithelial cells were purified as described (8).

PRL-3 (also known as PTP4A3) encodes a small 22 kD tyrosine phosphatase that is located at the cytoplasmic membrane when prenylated at its carboxyl terminus and in the nucleus when it is not conjugated to this lipid (12). Among normal human adult tissues, it is expressed predominantly in muscle and heart (13). Although PRL-3 had not been linked previously to human cancer, overexpression of PRL-3 has been found to enhance growth of human embryonic kidney fibroblasts (13) and overexpression of PRL-1 or PRL-2, close relatives of PRL-3, has been found to transform mouse fibroblasts and hamster pancreatic epithelial cells in culture and promote tumor growth in nude mice (14, 15). Based on this information, our preliminary expression data, and the importance of other phosphatases in cell signaling and neoplasia, we examined PRL-3 in greater detail. We first investigated PRL-3 expression in epithelial cells purified from colorectal tissues from various stages of colorectal neoplasia using the procedure described above (8); this purification proved essential for accurate quantification of its expression. PRL-3 was expressed at low levels in normal colorectal epithelium and epithelium from benign tumors (adenomas) and at intermediate levels in a subset of malignant Stage I or II cancers (FIG. 2). In contrast, it was expressed at relatively high levels in each of 12 colorectal cancer metastases (examples in FIG. 2).

Example 4

Consistent Correlation of Expression of PRL-3 in Several Patient Samples

Figure 3:
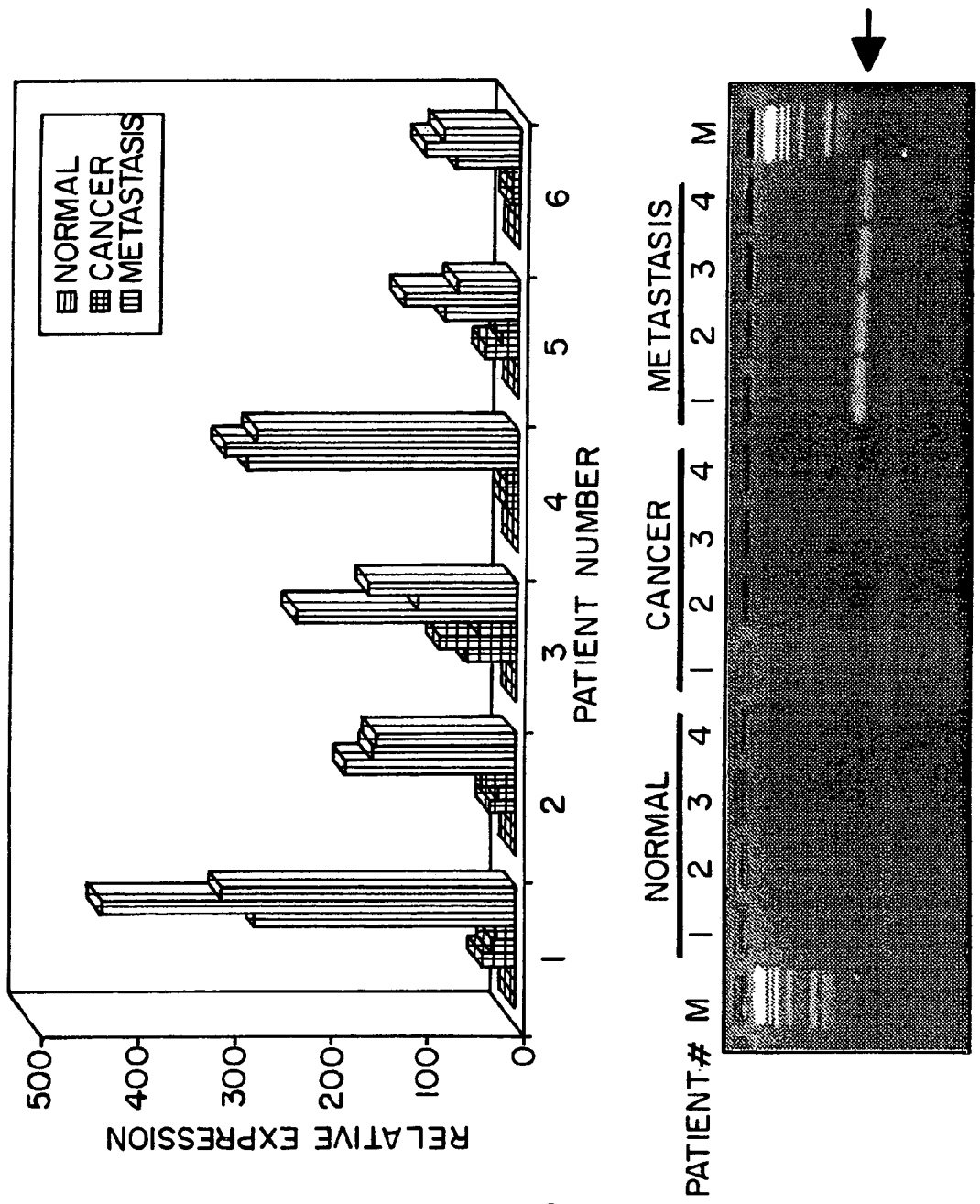
FIG. 3. PRL-3 expression in matched metastases and advanced primary cancers. Colonic epithelial cells were purified from a liver metastasis, a primary cancer giving rise to the metastasis, and normal colorectal epithelium from each of six patients (FIG. 3A) Gel of RT-PCR products from matched normal, primary cancer, and metastasis from four patients. Real-time PCR was performed for 24 cycles, when RT-PCR products from the metastases were evident but before signals from the other lesions had appeared. Arrow indicates the PRL-3 RT-PCR product of 198 bp.

The metastases evaluated in FIG. 2 were not derived from the same patients from whom the earlier stage lesions were obtained. Previous analyses have revealed that expression patterns of many genes differ between individuals, and that comparisons of tissues from different patients could potentially be misleading (16). To address this concern, we purified epithelial cells from a liver metastasis, the advanced (Stage III) colorectal cancer giving rise to the metastasis, and normal colorectal epithelium from each of six different patients. There was little or no expression in the normal epithelium from these cases, intermediate expression in the advanced primary cancers, and significantly higher expression in each of the matched metastatic lesions (FIG. 3).

Example 5

PRL-3 is Amplified in a Subset of Metastatic Lesions

The observation that PRL-3 is expressed at relatively high levels in metastases is consistent with its playing a causative role in metastasis. However, the most definitive way to implicate a gene in human cancer is to identify genetic alterations of that gene (17). We therefore determined whether PRL-3 was genetically altered through gene amplification, a well-known mechanism for increasing the expression of growth-regulating genes in human cancers (18). Through radiation hybrid and syntenic mapping, we found that the PRL-3 gene was located ~3 Mb from the telomere of chromosome 8q, at a position corresponding to chromosomal band 8q24.3 (19). Real-time PCR analyses of genomic DNA prepared from the purified epithelial cells of twelve metastatic lesions, each from a different patient, was performed to determine PRL-3 gene content; as with expression analyses, such purification proved critical for reliable quantification. In each case, we determined the genomic content of PRL-3 sequences relative to that of a sequence near the centromere of chromosome 8q (8). This comparison allowed us to distinguish true amplification from simple increases in chromosome number due to aneuploidy (18). We found that three of the twelve metastases studied exhibited amplification, to levels of ~25 copies, 26 copies, and 37 copies per diploid genome.

Example 6

PRL-3 is Only Known Expressed Gene in Amplicon

Figure 4:
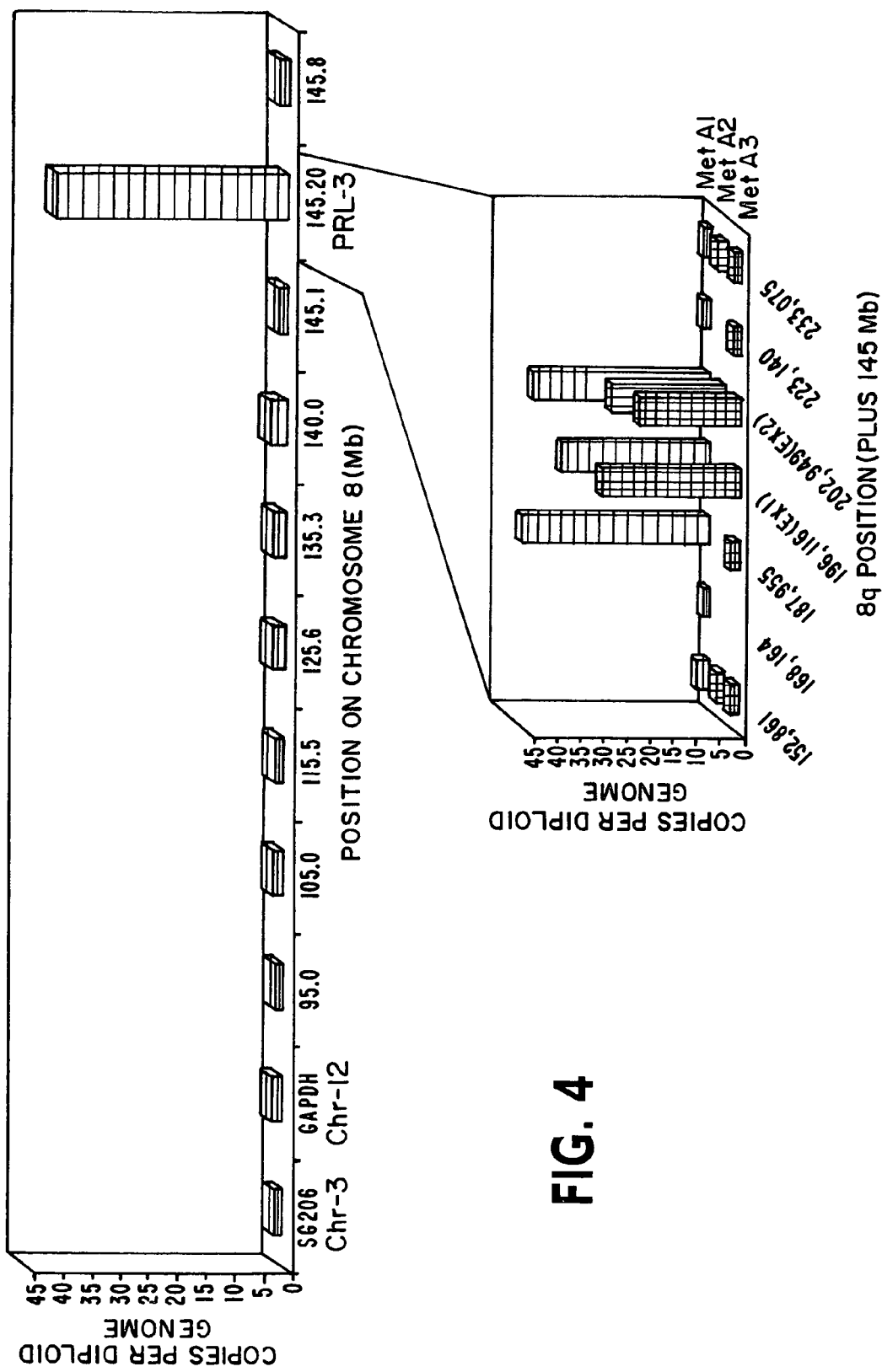
FIG. 4 Amplicon mapping of PRL-3. The number of copies of sequences corresponding to each of the indicated loci was determined using real-time PCR. In each case, the number of copies per diploid genome was determined by comparison to equal amounts of DNA from normal cells (8). Genomic DNA from purified epithelial cells of metastases from three different patients was used for these experiments; in another nine patients, no amplification of PRL-3 sequences was observed. The top panel depicts results obtained from one of the metastases, using primers corresponding to several chromosome 8q sequences as well as to sequences from two other chromosome arms as controls. The bottom panel indicates more detailed mapping of all three metastases, using primers corresponding to sequences within a small region ~145 Mb from the telomere of chromosome 8p (the centromere of chromosome 8 is at ~45 Mb). The positions indicated in the bottom panel refer to nucleotides distal to the 145 Mb position (e.g., "152,861" refers to a position 145,152,861 bp from the telomere of 8p). All three metastases were shown to lack amplification of proximal chromosome 8q sequences (at positions 95 and 135 Mb). Not all markers could be studied in all metastases because of the limited amounts of DNA obtained from purified epithelial cells of these lesions. Bars represent the averages of at least three independent determinations, and standard deviations were always <5% of the measured cycle numbers. Forward and reverse primers used for amplicon mapping are shown in Table 3, (SEQ ID NO: 157-173, and 174-190, respectively.

We next compared the genomic content of sequences distributed throughout chromosome 8q to define those that were amplified in these three metastases (8). The availability of the nearly complete human genomic sequence considerably facilitated this mapping effort (20, 21). Though the PRL-3 gene was not found in public databases generated through the Human Genome Project, it was found on a Celera scaffold located ~145 Mb from the telomere of chromosome 8p and ~3 Mb from the telomere of chromosome 8q, consistent with our radiation hybrid mapping data (19, 22) (FIG. 4). In all cases, amplification was confined to a very small region of chromosome 8q that included PRL-3 (FIG. 4) (22). The only known or predicted genes within this small amplicon were PRL-3 and a hypothetical gene homologous to a TATA-binding protein. No expression of the latter gene was detectable in metastatic lesions when assessed by RT-PCR. However, the region of the Celera scaffold on which PRL-3 maps (22) contains gaps estimated to be <20 kb in size. If these gaps were in fact larger than expected, the total size of the amplicon would be larger than the 100 kb indicated in FIG. 4 and could contain additional genes.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

TABLE 1

Selected genes upregulated in colon cancer metastasis

| SAGE TAG | Normal 1 | Normal 2 | Cancer 1 | Cancer 2 | Metastasis | Description |
|---|---|---|---|---|---|---|
| TAGGTCAGGA | 0 | 0 | 0 | 0 | 12 | protein tyrosine phosphatase type IVA (PRL-3) |
| TGATTGGTTT | 0 | 0 | 0 | 0 | 11 | cDNA: FLJ23603 |
| GGAATATGCA | 0 | 0 | 0 | 1 | 18 | LOC54675: hypothetical protein |
| AATCTTGTTT | 0 | 0 | 0 | 0 | 9 | hypothetical gene ZD52F10 |
| GTCTTCTTAA | 0 | 0 | 1 | 0 | 16 | DNAJ domain-containing |
| ATAATAAAAG | 0 | 0 | 1 | 1 | 30 | GRO3 oncogene/T45117 hU1-70K protein |
| TAAATATGGA | 0 | 0 | 0 | 0 | 7 | attractin |
| ATTTTTGTAT | 0 | 0 | 1 | 0 | 14 | Bcl-2 binding component 3 |
| TAGCTGGAAA | 4 | 0 | 0 | 1 | 67 | nuclear receptor subfamily 4 |
| GGAGGGCTGG | 0 | 0 | 1 | 0 | 13 | mitogen-activated protein kinase 8 interacting protein 2/ESTs similar to S26689 |

TABLE 1-continued

Selected genes upregulated in colon cancer metastasis

| SAGE TAG | Normal 1 | Normal 2 | Cancer 1 | Cancer 2 | Metastasis | Description |
|---|---|---|---|---|---|---|
| GTCAGTCACT | 1 | 0 | 0 | 0 | 13 | hairy (Drosophila)-homolog |
| TTGAGTAGGA | 1 | 0 | 1 | 0 | 23 | LUC7 (S. cerevisiae)-like |
| TGGGGGCCGA | 0 | 3 | 0 | 0 | 33 | transducin-like enhancer of split 2, homolog of Drosophila E (sp1) |
| TGGGCTGGGG | 0 | 0 | 2 | 1 | 32 | adipose differentiation-related protein |
| TAGCTGGAAC | 0 | 0 | 1 | 0 | 10 | ESTs, no known homologies |
| CTTCCTTGCC | 0 | 0 | 2 | 3 | 46 | keratin 17 |
| GCGGCAGTTA | 0 | 0 | 0 | 1 | 8 | casein kinase 2, alpha prime polypeptide |
| CTGCACTTAC | 1 | 0 | 2 | 3 | 46 | minichromosome maintenance deficient 7 (S. cerevisiae) |
| AAGCTGTTTA | 1 | 0 | 1 | 1 | 23 | v-jun avian sarcoma virus 17 oncogene homolog/ LSFR2 gene 2/MGC2550 protein |
| GTGAGGGCTA | 1 | 2 | 1 | 0 | 28 | plexin B1 |
| GGGGCTGTAT | 0 | 0 | 1 | 0 | 7 | transforming growth factor, beta 1 (TGF-β) |
| CTGGAGGCTG | 1 | 1 | 0 | 1 | 20 | ESTs, similar to GTP-rho binding protein 1 (rhophilin) |
| GGCTGGGTTT | 1 | 1 | 1 | 5 | 42 | H2.0 (Drosophila)-like homeo box 1 |
| GGGGGTGGGT | 1 | 0 | 0 | 1 | 10 | mago-nashi (Drosophila) homolog, proliferation-associated |
| CAGCATCTAA | 1 | 1 | 1 | 1 | 19 | putative Rab5-interacting protein |
| TTTCCAATCT | 0 | 0 | 0 | 4 | 18 | vascular endothelial growth factor |
| TTTCTAGGGG | 0 | 1 | 2 | 2 | 22 | PTD008 protein |
| AAAGTGAAGA | 1 | 0 | 3 | 5 | 37 | FLJ11328 protein/ribosomal protein L10 |
| TTTGCACTTG | 3 | 1 | 0 | 0 | 15 | wee1+ (S. pombe) homolog/protein x 013 |
| CCTGGAATGA | 1 | 0 | 0 | 3 | 15 | cDNA: FLJ12683 |
| GGAGGTAGGG | 1 | 0 | 3 | 0 | 15 | PTK7 protein tyrosine kinase 7 |
| CTGTACTTGT | 9 | 5 | 0 | 0 | 52 | v-fos FBJ murine osteosarcoma viral oncogene homolog B |
| TCCTTGCTTC | 1 | 1 | 3 | 1 | 22 | FLJ20297 protein |
| TATCTGTCTA | 0 | 0 | 2 | 5 | 25 | SET translocation (myeloid leukemia-associated) |
| TTAGATAAGC | 0 | 0 | 3 | 8 | 33 | chaperonin containing TCP1, subunit 6A (zeta 1) |
| AGTGGAGGGA | 1 | 0 | 1 | 1 | 9 | ataxin 2 related protein |
| TGCAGATATT | 0 | 0 | 2 | 1 | 8 | cyclin-dependent kinase inhibitor 3 (CDK2-associated dual specificity phosphatase) |
| GGGAGGGGTG | 1 | 1 | 2 | 2 | 14 | matrix metalloproteinase 14 (membrane-inserted) |

TABLE 2

Primers used to study selected genes upregulated in colon cancer metastasis by RT-PCR.

| SAGE TAG | Description | Forward Primer | Reverse Primer |
|---|---|---|---|
| TAGGTCAGGA | protein tyrosine phosphatase type IVA (PRL-3) | AGCCCCGTACTTCTTCAGGT | GGGACTTCTCAGGTCGTGTC |
| TGATTGGTTT | cDNA: FLJ23603 | CTCCACCCTTGAATTCCTGA | TTGCGCACACACACAAAATA |
| GGAATATGCA | LOC54675: hypothetical protein | CCCAGTTCTGGGCTATTTGA | AGCAGTGGCATAGCAAGGAT |
| AATCTTGTTT | hypothetical gene ZD52F10 | AGGCAATTTCTTGCAACCAC | CACCAAAGGGAGGAGGTACA |
| GTCTTCTTAA | DNAJ domain-containing | CCAGCAGGGACTGGTAAGAA | TCTTAGCCTTGCCAGCAGAT |
| ATAATAAAAG | GRO3 oncogene/T45117 hU1-70K protein | GCAGGGAATTCACCTCAAGA | CCTTTCCAGCTGTCCCTAGA |
| TAAATATGGA | attractin | AGGGGCTGATTCACTTCCTT | AGGATGGCCAATTCTCACAG |
| ATTTTTGTAT | Bcl-2 binding component 3 | AAGAGCAAATGAGCCAAACG | AATGAATGCCAGTGGTCACA |
| TAGCTGGAAA | nuclear receptor subfamily 4 | CACAGCTTGCTTGTCGATGT | TCTTGTCAATGATGGGTGGA |
| GGAGGGCTGG | mitogen-activated protein kinase 8 interacting protein 2/ESTs similar to S26689 | TCCCGAAGATGAAATGAAGG | CTCCAGGGGATCCTTGTA |
| GTCAGTCACT | hairy (Drosophila)-homolog | TGAGCCAGCTGAAAACACTG | GTGCGCACCTCGGTATTAAC |
| TTGAGTAGGA | LUC7 (S. cerevisiae)-like | TGCTGAATGTGATCGGAGAA | TGAACAGACCTCGCAGACAC |
| TGGGGGCCGA | transducin-like enhancer of split 2, homolog of Drosophila E (sp1) | TGAGTCTCATCCCCATCTCC | AGCAACTTGCAGGAACGAAT |
| TGGGCTGGGG | adipose differentiation-related protein | ACTGGCTGGTAGGTCCCTTT | ACGCCTTTTCAGATCACACC |
| TAGCTGGAAC | ESTs, no known homologies | ATAGGGCAGGTGGCATGTT | GGCAAGGGATCCAATTCTG |
| CTTCCTTGCC | keratin 17 | CGGAGACAGAGAACCGCTAC | CACAATGGTACGCACCTGAC |
| GCGGCAGTTA | casein kinase 2, alpha prime polypeptide | GTGCAGACAATGCTGTGCTT | CCTTCGCTTGGTCTAGTTCG |
| CTGCACTTAC | minichromosome maintenance deficient 7 (S. cerevisiae) | CGGTGCTGGTAGAAGGAGAG | TTTCATGCCTCGAGGAGACT |
| AAGCTGTTTA | v-jun avian sarcoma virus 17 oncogene homolog/LSFR2 gene 2/MGC2550 protein | GGCAGACAGACAGACACAGC | GAGAAGCCTAAGACGCAGGA |
| GTGAGGGCTA | plexin B1 | ACAAGGTGTATGCGGAGAGG | ATACTGGGCAACCAGGTCAC |
| GGGGCTGTAT | transforming growth factor, beta 1 | GGCCCTGTACAACCAGCATA | GGGCACGGTGTCCTTAAATA |
| CTGGAGGCTG | ESTs, similar to GTP-rho binding protein 1 (rhophilin) | CCCAGCTCTAGACTGCCAAG | CTGGGTGCTTCAAGGATGAG |
| GGCTGGGTTT | H2.0 (Drosophila)-like homeo box 1 | GAGGCTTTCTGCAATCCTGAG | AGCCTCCTTGTCCTTGTCCT |
| GGGGGTGGGT | mago-nashi (Drosophila) homolog, proliferation-associated | GGAGCCATGGAGAGTGACTT | CCTTCTGGATCCTTGGATTG |
| CAGCATCTAA | putative Rab5-interacting protein | TTGGGGAGTTTTGCCATTAC | TTGGACTGGATAGGGAGCAC |
| TTTCCAATCT | vascular endothelial growth factor | GGGCAGAATCATCACGAAGT | CCTTTCCCTTTCCTCGAACT |
| TTTCTAGGGG | PTD008 protein | TCTCCGTTCTCTGGGTAAGG | GCACATGCTGAAGATCATGC |
| AAAGTGAAGA | FLJ11328 protein/ribosomal protein L10 | TCCCACCCTCAATATCCTCA | CCTGGTCACTCCAAGTCCAT |
| TTTGCACTTG | wee1+ (S. pombe) homolog/protein x 013 | AGACCTTCAGCAATGGCACT | GCGGTTCATTTTCTTTCCAA |
| CCTGGAATGA | cDNA: FLJ12683 | AGGGAGAGTCCCTCCACTGT | TTGATTCCTTTCCCACAAGC |
| GGAGGTAGGG | PTK7 protein tyrosine kinase 7 | CTGAAGAAGCCCCAAGACAG | ACGGTACCATGTCCCATCAT |
| CTGTACTTGT | v-fos FBJ murine osteosarcoma viral oncogene homolog B | ATTGGAATTTCTGGCCTCCT | TTCTGTCACCCCCTTGAGTC |
| TCCTTGCTTC | FLJ20297 protein | AGCCTCTGTCATGAGGAACG | GCCCAGCAGGTTCATGTAGT |
| TATCTGTCTA | SET translocation (myeloid leukemia-associated) | GGGAGCAAGTTGCAGTCTTT | CCACCCAAACATCTCAAACC |

TABLE 2-continued

Primers used to study selected genes upregulated in colon cancer metastasis by RT-PCR.

| SAGE TAG | Description | Forward Primer | Reverse Primer |
|---|---|---|---|
| TTAGATAAGC | chaperonin containing TCP1, subunit 6A (zeta 1) | GCCCTGAATTCTTTTGACGA | TCCCATACGCCTACTTCTGC |
| AGTGGAGGGA | ataxin 2 related protein | TGAGGGTTCTGGCTTACTGG | CTGGGAGGGATGAGATTGAA |
| TGCAGATATT | cyclin-dependent kinase inhibitor 3 (CDK2-associated dual specificity phosphatase) | CCGCCCAGTTCAATACAAAC | TCTATGGCTTGCTCTGGTGA |
| GGGAGGGGTG | matrix metalloproteinase 14 (membrane-inserted) | CATGGCACCCTTTTACCAGT | GCATTGGGTATCCATCCATC |

TABLE 3

Primers used to map the PRL-3 amplicon by genomic PCR.

| Primer Set | Forward Primer | Reverse Primer |
|---|---|---|
| 95.0 Mb | GGGCTTCCCTAAGCACAAAT | TTAGGCGGAGTCTTGAGGAA |
| 105.0 Mb | CGGTTTCCTTACTGACCTGCT | CCAACAGGATACCTGAAGCAA |
| 115.5 Mb | ACTTTGGGAGGCTGAGACAG | CCTCCTGAGCAGCTGAGATT |
| 125.6 Mb | TTGCCATTCTGTACACCTGAA | GACAATTGGCAAAATTGGAA |
| 135.3 Mb | CGAAGGCACGTTTCCTTAGA | AAGCTCCCTGAGGAGAGACA |
| 140.0 Mb | GGGCTCACAAGACAGGAAGA | CTCCAGTTCCCAGCAAGTTC |
| 145.1 Mb | CCTCTTACTCCCCCTCACCT | TGGTGGCTTCTGAGTGTTCA |
| 145.8 Mb | GCCAGGGTCAGTGATTCTTC | GGTCACCCATTCTAGCCTCA |
| 145,152,861 Mb | GGAAGGCTGTGGGTCTCATA | CTTGAGGAGCACCTGTCAGA |
| 145,168,164 Mb | CAGGCCTTTGTCCTGATCC | GCCCTGGGGAGCTACAAG |
| 145,187,955 Mb | CCACATGCTGGCATCTCTAC | GTGAGCCAGGCATCCTACAT |
| 145,198,116 Mb | CCTCACAGAACTTGGCCTTC | GCCTCTCTACCCTCCCTCAG |
| 145,202,949 Mb | GGGACACGACCTGAGAAGTC | AATATTTGTGCGGGGTATGG |
| 145,223,140 Mb | TCACAGGTACCGTTGGTTGA | AAGTGGGACGAACACCTGTC |
| 145,233,075 Mb | AGGGCCGAGTTTTGTTTGTT | TTTAGGACACACCCGACCAT |
| SG206 (Chr-3) | GGAATTACAAGGAAGTGCCAAT | ATCGACCACAGAAGGCATTT |
| GAPDH (Chr-12) | AAAGGGCCCTGACAACTCTT | GGTGGTCCAGGGGTCTTACT |

REFERENCES AND NOTES

1. L. Weiss, *Cancer Metastasis Rev.* 19, 193 (2000).
2. I. J. Fidler, *Surg. Oncol. Clin. N. Am.* 10, 257, vii (2001).
3. A. Ridley, *Nature* 406, 466 (2000).
4. K. W. Kinzler, B. Vogelstein, *Cell* 87, 159 (1996).
5. V. E. Velculescu, B. Vogelstein, K. W. Kinzler, *Trends Genet.* 16, 423 (2000).
6. SAGE libraries were generated using MicroSAGE. Reagents for this procedure were obtained from the I-SAGE kit available from Invitrogen (Carlsbad, Calif.).
7. Examples of the non-epithelial transcripts identified in the initial libraries were vitronectin and lysozyme. These genes are transcribed in stromal cells, and accounted for 0.4% and 0.1%, respectively, of the tags in SAGE libraries prepared from unpurified metastatic lesions but were not found in the SAGE library derived from purified metastatic epithelial cells. Similarly, transcripts made in hepatocytes, like apolipoprotein C-III, accounted for 0.3% of the tags from unpurified metastasis libraries but were not found in the libraries from purified cells. These differences in vitronectin, lysozyme, and apolipoprotein C-III expression among SAGE libraries derived from purified and unpurified epithelial cells were statistically significant (p<0.0001, $\chi^2$ test).
8. Methods used in this study, including those used for purification of epithelial cells, are described in supplementary web material available on Science Online at www.sciencemag.org.
9. V. E. Velculescu et al., *Nature Genet.* 23, 387 (1999).
10. The metastasis-derived library was compared to two primary colorectal cancer and two normal colorectal epithelial libraries (L. Zhang et al., *Science* 276, 1268 (1997)). Monte Carlo simulations were used to identify transcripts that were expressed in the metastasis library at levels 10-fold higher or 10-fold lower than in the other libraries, with P-chance <0.0001, as described in V. E. Velculescu, L. Zhang, B. Vogelstein, K. W. Kinzler, *Science* 270, 484 (1995). A complete listing of the SAGE tags and corresponding transcripts identified in this study is available at www.sagenet.org.
11. The transcripts chosen for further analysis included those for which the SAGE data indicated at least 10-fold greater expression in metastatic versus non-metastatic lesions or for which the predicted gene products had potentially interesting functional properties.
12. Q. Zeng et al., *J. Biol. Chem.* 275, 21444 (2000).
13. W. F. Matter et al., *Biochem. Biophys. Res. Commun.* 283, 1061 (2001).
14. R. H. Diamond, D. E. Cressman, T. M. Laz, C. S. Abrams, R. Taub, *Mol. Cell. Biol.* 14, 3752 (1994).
15. C. A. Cates et al., *Cancer Lett.* 110, 49 (1996).
16. C. M. Perou et al., *Nature* 406, 747 (2000).
17. D. Haber, E. Harlow, *Nature Genet.* 16, 320 (1997).
18. G. M. Brodeur, M. D. Hogarty, in *The Genetic Basis of Human Cancer* K. W. Kinzler, B. Vogelstein, Eds. (McGraw-Hill, New York, 1998), vol. 1, pp. 161-179.
19. The mouse homolog of PRL-3 was mapped to a region of mouse chromosome 15 (23135.11cR on Chr. 15 WI-RH Map (cR3000)) that is syntenic to the human 8q22-8q24.3 (http://Hwww.ncbi.nlm.nih.gov/Homology/view.cgi?chr=15&tax_id=10090). STS primers from the PRL-3 gene and surrounding marker 145.8 (FIG. 4) were mapped to the Stanford G3 radiation hybrid panel. Both were shown be tightly linked to marker SHGC-22154, located at 8q24.3, approximately 3 Mb from the 8q telomere. In comparison, c-Myc was mapped to 8q24.12-q24.13 in the Stanford G3 map, approximately 17 Mb from the telomere.
20. J. C. Venter et al., *Science* 291, 1304 (2001).
21. E. S. Lander et al., *Nature* 409, 860 (2001).
22. The PRL-3 transcript (GenBank Accesssion # NM_032611) could not be identified in the Human Genome Project draft genome sequences, using standard tools including BLAST searches against draft genome sequence (National Center for Biotechnology Information) and against assembled draft sequences. However, the PRL-3 transcript was identical to Celera transcript hCT11716 and was found on Celera scaffold GA_x2KMHMRCHQ1, CHGD Assembly Release 25h.
23. M. A. Heiskanen et al., *Cancer Res.* 60, 799 (2000).
24. M. D. Pegram, G. Konecny, D. J. Slamon, *Cancer Treat. Res.* 103, 57 (2000).
25. J. C. Alers et al., *Lab Invest.* 77, 437 (1997).
26. A. Paredes-Zaglul et al., *Clin. Cancer Res.* 4, 879 (1998).
27. N. N. Nupponen, J. Isola, T. Visakorpi, *Genes Chromosomes Cancer* 28, 203 (2000).
28. A. El Gedaily et al., *Prostate* 46, 184 (2001).29. B. Vogelstein, D. Lane, A. J. Levine, *Nature* 408, 307 (2000).

We claim:

1. A method to identify candidate drugs useful for treating advanced or metastatic tumors, comprising:
   determining the ability of a test compound to inhibit PRL-3 activity;
   identifying a test compound which inhibits PRL-3 activity as a compound potentially useful in treating advanced or metastatic tumors;
   testing the compound which inhibits PRL-3 activity for the ability to inhibit growth of cancer cells in vitro, wherein the cancer cells are selected from the group consisting of gastrointestinal, colorectal, and cancer cells that have metastasized to the liver.

2. The method of claim 1 wherein the step of determining utilizes DiFMuP (6,8-difluoro-4-methylumbelliferyl phosphate) as a substrate of PRL-3 in an enzyme assay.

3. The method of claim 1 wherein the step of determining utilizes p130$^{cas}$ as a substrate of PRL-3 in an enzyme assay.

4. The method of claim 1 wherein the cancer cells are gastrointestinal cancer cells.

5. The method of claim 1 wherein the cancer cells are colorectal cancer cells.

6. The method of claim 1 wherein the cancer cells are cancer cells that have metastasized to the liver.

7. The method of claim 1 wherein the test compound is tested for its ability to inhibit PRL-3 relative to an enzyme selected from the group consisting of PRL-2 and PRL-1.

8. The method of claim 1 wherein the step of determining uses an enzyme assay.

9. The method of claim 1 wherein the step of determining uses a substrate of PRL-3 selected from the group consisting of DiFMuP (6,8-difluoro-4-methylumbelliferyl phosphate), p130$^{cas}$ and histone 2B, in an enzyme assay.

10. A method to identify candidate drugs useful for treating advanced or metastatic tumors, comprising:
    determining the ability of a test compound to inhibit PRL-3 activity;
    identifying a test compound which inhibits PRL-3 activity as a compound potentially useful in treating advanced or metastatic tumors; and
    testing in vivo the compound which inhibits PRL-3 for the ability to inhibit progression of a tumor in an experimental animal, wherein the tumor is selected from the group consisting of gastrointestinal cancer and colorectal cancer.

11. The method of claim 10 wherein the tumor is a gastrointestinal tumor.

12. The method of claim 10 wherein the tumor is a colorectal tumor.

13. The method of claim 10 wherein the step of testing comprises administering the compound to the experimental animal.

14. The method of claim 10 wherein the step of determining uses an enzyme assay.

15. The method of claim 10 wherein the step of determining uses a substrate of PRL-3 selected from the group consisting of DiFMuP (6,8-difluoro-4-methylumbelliferyl phosphate), p130$^{cas}$, and histone 2B, in an enzyme assay.

16. A method to identify candidate drugs useful for treating advanced or metastatic tumors, comprising:

determining the ability of a test compound to inhibit PRL-3 activity;

identifying a test compound which inhibits PRL-3 activity as a compound potentially useful in treating advanced or metastatic tumors; and testing in vivo the compound which inhibits PRL-3 for the ability to inhibit metastasis of a colorectal tumor in an experimental animal.

17. The method of claim 16 wherein the step of testing comprises administering the compound to the experimental animal.

18. The method of claim 16 wherein the step of determining uses an enzyme assay.

19. The method of claim 16 wherein the step of determining uses a substrate of PRL-3 selected from the group consisting of DiFMuP (6,8-difluoro-4-methylumbelliferyl phosphate), p130$^{cas}$, and histone 2B, in an enzyme assay.

* * * * *